US011459543B2

(12) United States Patent
Sun

(10) Patent No.: US 11,459,543 B2
(45) Date of Patent: Oct. 4, 2022

(54) RECOMBINANT CHIMERIC ANTIGEN RECEPTOR GENE AND USE THEREOF

(71) Applicant: YIMING (BEIJING) CELL BIOTECH LTD., Beijing (CN)

(72) Inventor: Xiulian Sun, Shandong (CN)

(73) Assignee: YIMING (BEIJING) CELL BIOTECH LTD., Beijing (CN)

( * ) Notice: Subject to any disclaimer, the term of this patent is extended or adjusted under 35 U.S.C. 154(b) by 711 days.

(21) Appl. No.: 16/193,473

(22) Filed: Nov. 16, 2018

(65) Prior Publication Data

US 2019/0249142 A1    Aug. 15, 2019

Related U.S. Application Data

(63) Continuation of application No. PCT/CN2018/076801, filed on Feb. 14, 2018.

(51) Int. Cl.
*C12N 5/0783* (2010.01)
*C12N 15/62* (2006.01)
*C07K 16/28* (2006.01)
*A61P 35/00* (2006.01)

(52) U.S. Cl.
CPC ........ *C12N 5/0636* (2013.01); *C07K 16/2809* (2013.01); *C07K 16/2818* (2013.01); *C07K 16/2875* (2013.01); *C07K 16/2878* (2013.01); *C12N 15/62* (2013.01); *A61P 35/00* (2018.01); *C07K 2317/622* (2013.01); *C07K 2319/03* (2013.01); *C07K 2319/33* (2013.01)

(58) Field of Classification Search
CPC .............. C12N 5/0636; C07K 16/2878; C07K 2317/622; C07K 2319/33; C07K 2319/03; A61P 35/00
See application file for complete search history.

(56) References Cited

U.S. PATENT DOCUMENTS

2016/0046724 A1* 2/2016 Brogdon ............ C07K 16/2878
                                                          435/328

FOREIGN PATENT DOCUMENTS

| CN | 107312097    | 11/2011 |           |
|----|--------------|---------|-----------|
| CN | 105950663    | 5/2016  |           |
| CN | 105859890    | 8/2016  |           |
| CN | 105859890 A  | 8/2016  |           |
| CN | 105924527 A  | 9/2016  |           |
| CN | 105950663 A *| 9/2016  | A61K 35/17|
| CN | 107312097 A  | 11/2017 |           |
| CN | 106086078    | 12/2017 |           |
| WO | WO-2015028444 A1 * | 3/2015 | A61K 35/17 |
| WO | WO 2017/190100 | 11/2017 |          |

OTHER PUBLICATIONS

Brudno, Jennifer N., et at "Chimeric Antigen Receptor T-cell Therapies for Lymphoma," Nature Reviews, Clinical Onclology, vol. 15, Jan. 2018: pp. 31-46.
Ngo, Minhtran C., et al. "Ex Vivo Gene Transfer for Improved Adoptive Immunotherapy of Cancer," *Human Molecular Genetics* 20.R1 (2011): R93-R99.
Office Action dated Feb. 26, 2019 for corresponding CN Patent No. 201810707905.0.
Office Action dated Apr. 9, 2019 for corresponding CN Patent No. 201810707905.0.
Office Action dated May 24, 2019 for corresponding CN Patent No. 201810707905.0.
Search Report dated Jan. 2, 2019 for corresponding CN Patent No. 201810707905.0.
Tumaini, Barbara, et al., "Simplified Process for the Production of Anti-CD19-CAR engineered T Cells," *Cytotherapy* 15.11 (2013): 1406-1415.
International Search Report for corresponding PCT Application No. PCT/CN2018/076801 dated Nov. 6, 2018.
Kalos Michael et al. " Adoptive T Cell Transfer for Cancer Immunotherapy in the Era of Synthetic Biology" Jul. 25, 2013 ª 2013 Elsevier Inc.
Klimka et al. "Human anti-CD30 recombinant antibodies by guided phage antibody selection using cell panning" Laboratory of Immunotherapy, British Journal of Cancer (2000) 83(2), 252-260.
Hornbach Andreas et al. "Characterization of a Chimeric T-Cell Receptor with Specificity for the Hodgkin's Lymphoma-Associated CD30 Antigen" Journal of Immunotherapy 22(6):473-480 © 1999 Lippincott Williams & Wilkins, Inc., Philadelphia.
Van der stegen Sjoukje J.C. et al. "The pharmacology of second-generation chimeric antigen receptors" Nature Reviews | Drug Discovery vol. 14; Jul. 2015| 499-509.
Wang Zhenguang et al. "Biomarkers of cytokine release syndrome and neurotoxicity related to CAR-T cell therapy" Wang and Han Biomarker Research (2018) 6:4 p. 1-10.

* cited by examiner

*Primary Examiner* — Amy E Juedes
*Assistant Examiner* — Brian Hartnett
(74) *Attorney, Agent, or Firm* — Mark S. Cohen; Pearl Cohen Zedek Latzer Baratz LLP

(57) ABSTRACT

The invention provides a recombinant chimeric antigen receptor (CAR) gene, a vector containing the same, a CAR-T cell and a use thereof. The recombinant CAR gene comprises a nucleic acid sequence encoding an antigen-binding portion of a CD30 antibody, a transmembrane portion and a CD137 cytoplasmic functional region and a CD3zeta cytoplasmic functional region linked in any order; also provides a method of treating Hodgkin's lymphoma or anaplastic large cell lymphoma or other CD30-positive tumors using the CAR-T cells of the invention.

2 Claims, 4 Drawing Sheets
Specification includes a Sequence Listing.

SEQUENCE LISTING

<160> NUMBER OF SEQ ID NOS: 31

<210> SEQ ID NO 1
<211> LENGTH: 120
<212> TYPE: PRT
<213> ORGANISM: Artificial Sequence
<220> FEATURE:
<223> OTHER INFORMATION: VH

<400> SEQUENCE: 1

Gln Val Gln Leu Gln Gln Ser Gly Ala Glu Val Lys Lys Pro Gly Ser
1               5                   10                  15

Ser Val Lys Val Ser Cys Lys Thr Ser Gly Tyr Thr Phe Thr Gly Tyr
            20                  25                  30

Tyr Met His Trp Val Arg Gln Ala Pro Gly Gln Gly Phe Glu Trp Met
        35                  40                  45

Gly Trp Ile Asp Pro Asn Ser Gly Ala Thr Thr Tyr Ala Gln Lys Phe
    50                  55                  60

```
Gln Gly Arg Leu Ile Leu Ser Arg Asp Thr Ser Ile Asn Thr Ala Tyr
 65                  70                  75                  80

Met Glu Leu Arg Arg Leu Thr Ser Asp Asp Thr Ala Val Tyr Tyr Cys
                 85                  90                  95

Ala Lys Lys Thr Thr Gln Thr Thr Trp Gly Phe Pro Phe Trp Gly Gln
            100                 105                 110

Gly Thr Thr Val Thr Val Ser Ser
            115                 120

<210> SEQ ID NO 2
<211> LENGTH: 108
<212> TYPE: PRT
<213> ORGANISM: Artificial Sequence
<220> FEATURE:
<223> OTHER INFORMATION: VL

<400> SEQUENCE: 2

Asp Ile Val Met Thr Gln Ser Pro Ser Thr Leu Ser Ala Ser Val Gly
  1               5                  10                  15

Asp Arg Val Thr Ile Thr Cys Arg Ala Ser Gln Gly Val Tyr Gln Trp
             20                  25                  30

Leu Ala Trp Tyr Gln Gln Lys Pro Gly Lys Ala Pro Asn Leu Leu Ile
         35                  40                  45

Tyr Lys Ala Ser His Leu Tyr Asn Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Asp Asp Phe Ala Thr Tyr Tyr Cys Gln Gln Leu Asn Ser Tyr Pro Leu
                 85                  90                  95

Thr Phe Gly Gly Gly Thr Lys Val Glu Ile Lys Arg
            100                 105

<210> SEQ ID NO 3
<211> LENGTH: 244
<212> TYPE: PRT
<213> ORGANISM: Artificial Sequence
<220> FEATURE:
<223> OTHER INFORMATION: scFv VL-linker-VH

<400> SEQUENCE: 3

Asp Ile Val Met Thr Gln Ser Pro Ser Thr Leu Ser Ala Ser Val Gly
  1               5                  10                  15

Asp Arg Val Thr Ile Thr Cys Arg Ala Ser Gln Gly Val Tyr Gln Trp
             20                  25                  30

Leu Ala Trp Tyr Gln Gln Lys Pro Gly Lys Ala Pro Asn Leu Leu Ile
         35                  40                  45

Tyr Lys Ala Ser His Leu Tyr Asn Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Asp Asp Phe Ala Thr Tyr Tyr Cys Gln Gln Leu Asn Ser Tyr Pro Leu
                 85                  90                  95

Thr Phe Gly Gly Gly Thr Lys Val Glu Ile Lys Arg Gly Gly Gly Ser
            100                 105                 110

Gly Gly Gly Ser Gly Gly Gly Ser Gly Gly Gly Ser Gln Val Gln Leu
            115                 120                 125

Gln Gln Ser Gly Ala Glu Val Lys Lys Pro Gly Ser Ser Val Lys Val
```

```
                130                 135                 140
Ser Cys Lys Thr Ser Gly Tyr Thr Phe Thr Gly Tyr Tyr Met His Trp
145                 150                 155                 160

Val Arg Gln Ala Pro Gly Gln Gly Phe Glu Trp Met Gly Trp Ile Asp
                165                 170                 175

Pro Asn Ser Gly Ala Thr Thr Tyr Ala Gln Lys Phe Gln Gly Arg Leu
                180                 185                 190

Ile Leu Ser Arg Asp Thr Ser Ile Asn Thr Ala Tyr Met Glu Leu Arg
                195                 200                 205

Arg Leu Thr Ser Asp Asp Thr Ala Val Tyr Tyr Cys Ala Lys Lys Thr
                210                 215                 220

Thr Gln Thr Thr Trp Gly Phe Pro Phe Trp Gly Gln Gly Thr Thr Val
225                 230                 235                 240

Thr Val Ser Ser

<210> SEQ ID NO 4
<211> LENGTH: 21
<212> TYPE: PRT
<213> ORGANISM: Homo sapiens

<400> SEQUENCE: 4

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 5
<211> LENGTH: 87
<212> TYPE: PRT
<213> ORGANISM: Homo sapiens

<400> SEQUENCE: 5

Ala Leu Ser Asn Ser Ile Met Tyr Phe Ser His Phe Val Pro Val Phe
1               5                   10                  15

Leu Pro Ala Lys Pro Thr Thr Thr Pro Ala Pro Arg Pro Pro Thr Pro
                20                  25                  30

Ala Pro Thr Ile Ala Ser Gln Pro Leu Ser Leu Arg Pro Glu Ala Cys
            35                  40                  45

Arg Pro Ala Ala Gly Gly Ala Val His Thr Arg Gly Leu Asp Phe Ala
        50                  55                  60

Cys Asp Ile Tyr Ile Trp Ala Pro Leu Ala Gly Thr Cys Gly Val Leu
65                  70                  75                  80

Leu Leu Ser Leu Val Ile Thr
                85

<210> SEQ ID NO 6
<211> LENGTH: 42
<212> TYPE: PRT
<213> ORGANISM: Homo sapiens

<400> SEQUENCE: 6

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
                20                  25                  30

Pro Glu Glu Glu Glu Gly Gly Cys Glu Leu
            35                  40
```

<210> SEQ ID NO 7
<211> LENGTH: 112
<212> TYPE: PRT
<213> ORGANISM: Homo sapiens

<400> SEQUENCE: 7

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 8
<211> LENGTH: 227
<212> TYPE: PRT
<213> ORGANISM: Homo sapiens

<400> SEQUENCE: 8

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 9
<211> LENGTH: 8736
<212> TYPE: DNA
<213> ORGANISM: Artificial Sequence
<220> FEATURE:
<223> OTHER INFORMATION: CAR-T30

<400> SEQUENCE: 9

| | | | | | |
|---|---|---|---|---|---|
| gtcgacggat | cgggagatct | cccgatcccc | tatggtgcac | tctcagtaca | atctgctctg | 60 |
| atgccgcata | gttaagccag | tatctgctcc | ctgcttgtgt | gttggaggtc | gctgagtagt | 120 |
| gcgcgagcaa | aatttaagct | acaacaaggc | aaggcttgac | cgacaattgc | atgaagaatc | 180 |
| tgcttagggt | taggcgtttt | gcgctgcttc | gcgatgtacg | ggccagatat | cgcgttgaca | 240 |
| ttgattattg | actagttatt | aatagtaatc | aattacgggg | tcattagttc | atagcccata | 300 |
| tatggagttc | cgcgttacat | aacttacggt | aaatggcccg | cctggctgac | cgcccaacga | 360 |
| cccccgccca | ttgacgtcaa | taatgacgta | tgttcccata | gtaacgccaa | tagggacttt | 420 |
| ccattgacgt | caatgggtgg | agtatttacg | gtaaactgcc | cacttggcag | tacatcaagt | 480 |
| gtatcatatg | ccaagtacgc | cccctattga | cgtcaatgac | ggtaaatggc | ccgcctggca | 540 |
| ttatgcccag | tacatgacct | tatgggactt | tcctacttgg | cagtacatct | acgtattagt | 600 |
| catcgctatt | accatggtga | tgcggttttg | gcagtacatc | aatgggcgtg | gatagcggtt | 660 |
| tgactcacgg | ggatttccaa | gtctccaccc | cattgacgtc | aatgggagtt | tgttttggca | 720 |
| ccaaaatcaa | cgggactttc | caaaatgtcg | taacaactcc | gccccattga | cgcaaatggg | 780 |
| cggtaggcgt | gtacggtggg | aggtctatat | aagcagcgcg | ttttgcctgt | actgggtctc | 840 |
| tctggttaga | ccagatctga | gcctgggagc | tctctggcta | actagggaac | ccactgctta | 900 |
| agcctcaata | aagcttgcct | tgagtgcttc | aagtagtgtg | tgcccgtctg | ttgtgtgact | 960 |
| ctggtaacta | gagatccctc | agacccttttt | agtcagtgtg | gaaaatctct | agcagtggcg | 1020 |
| cccgaacagg | gacttgaaag | cgaaagggaa | accagaggag | ctctctcgac | gcaggactcg | 1080 |
| gcttgctgaa | gcgcgcacgg | caagaggcga | ggggcggcga | ctggtgagta | cgccaaaaat | 1140 |
| tttgactagc | ggaggctaga | aggagagaga | tgggtgcgag | agcgtcagta | ttaagcgggg | 1200 |
| gagaattaga | tcgcgatggg | aaaaaattcg | gttaaggcca | gggggaaaga | aaaaatataa | 1260 |
| attaaaacat | atagtatggg | caagcaggga | gctagaacga | ttcgcagtta | atcctggcct | 1320 |
| gttagaaaca | tcagaaggct | gtagacaaat | actgggacag | ctacaaccat | cccttcagac | 1380 |
| aggatcagaa | gaacttagat | cattatataa | tacagtagca | accctctatt | gtgtgcatca | 1440 |
| aaggatagag | ataaaagaca | ccaaggaagc | tttagacaag | atagaggaag | agcaaaacaa | 1500 |
| aagtaagacc | accgcacagc | aagcggccgg | ccgctgatct | tcagacctgg | aggaggagat | 1560 |
| atgagggaca | attggagaag | tgaattatat | aaatataaag | tagtaaaaat | tgaaccatta | 1620 |
| ggagtagcac | ccaccaaggc | aaagagaaga | gtggtgcaga | gagaaaaaag | agcagtggga | 1680 |
| ataggagctt | tgttccttgg | gttcttggga | gcagcaggaa | gcactatggg | cgcagcgtca | 1740 |
| atgacgctga | cggtacaggc | cagacaatta | ttgtctggta | tagtgcagca | gcagaacaat | 1800 |
| ttgctgaggg | ctattgaggc | gcaacagcat | ctgttgcaac | tcacagtctg | gggcatcaag | 1860 |
| cagctccagg | caagaatcct | ggctgtggaa | agatacctaa | aggatcaaca | gctcctgggg | 1920 |
| atttggggtt | gctctggaaa | actcatttgc | accactgctg | tgccttggaa | tgctagttgg | 1980 |

```
agtaataaat ctctggaaca gatttggaat cacacgacct ggatggagtg ggacagagaa    2040
attaacaatt acacaagctt aatacactcc ttaattgaag aatcgcaaaa ccagcaagaa    2100
aagaatgaac aagaattatt ggaattagat aaatgggcaa gtttgtggaa ttggttaac    2160 ataacaaatt ggctgtggta tataaaatta ttcataatga tagtaggagg cttggtaggt    2220
ttaagaatag ttttttgctgt actttctata gtgaatagag ttaggcaggg atattcacca    2280
ttatcgtttc agaccacct cccaacccg aggggacccg acaggcccga aggaatagaa    2340
gaagaaggtg gagagagaga cagagacaga tccattcgat tagtgaacgg atcggcactg    2400
cgtgcgccaa ttctgcagac aaatggcagt attcatccac aatttaaaa gaaaagggg    2460 gattgggggg tacagtgcag gggaaagaat agtagacata atagcaacag acatacaaac    2520
taaagaatta caaaaacaaa ttacaaaaat tcaaaatttt cgggttatt acagggacag    2580 cagagatcca gtttggttag taccgggccc gctctagacg tgaggctccg gtgcccgtca    2640
gtgggcagag cgcacatcgc ccacagtccc cgagaagttg tggggagggg tcggcaattg    2700
aaccggtgcc tagagaaggt ggcgcggggt aaactgggaa agtgatgtcg tgtactggct    2760
ccgccttttt cccgagggtg ggggagaacc gtatataagt gcagtagtcg ccgtgaacgt    2820 tcttttcgc aacgggttg ccgccagaac acaggtaagt gccgtgtgtg gttcccgcgg    2880
gcctggcctc tttacgggtt atggcccttg cgtgccttga attacttcca cctggctgca    2940
gtacgtgatt cttgatcccg agcttcgggt tggaagtggg tggagagtt cgaggccttg    3000 cgcttaagga gccccttcgc ctcgtgcttg agttgaggcc tggcctgggc gctggggccg    3060
ccgcgtgcga atcggtggc accttcgcgc ctgtctcgct gctttcgata agtctctagc    3120
catttaaaat ttttgatgac ctgctgcgac gcttttttc tggcaagata gtcttgtaaa    3180
tgcgggccaa gatctgcaca ctggtatttc ggttttggg gccgcgggcg gcgacggggc    3240
ccgtgcgtcc cagcgcacat gttcggcgag gcggggcctg cgagcgcggc caccgagaat    3300 cggacgggg tagtctcaag ctggccgcc tgctctggtg cctggcctcg cgccgccgtg    3360
tatcgccccg ccctgggcgg caaggctggc ccggtcggca ccagttgcgt gagcggaaag    3420
atggccgctt cccggccctg ctgcagggag ctcaaaatgg aggacgcggc gctcgggaga    3480
gcgggcgggt gagtcaccca cacaaaggaa aagggccttt ccgtcctcag ccgtcgcttc    3540
atgtgactcc acggagtacc gggcgccgtc caggcacctc gattagttct cgagcttttg    3600
gagtacgtcg tctttaggtt gggggagg gttttatgcg atggagttc cccacactga    3660 gtgggtggag actgaagtta ggccagcttg gcacttgatg taattctcct tggaatttgc    3720
cctttttgag tttggatctt ggttcattct caagcctcag acagtggttc aaagtttttt    3780
tcttccattt caggtgtcgt gaggaatcct ctaggtcgac ctggatccgg taccgaggag    3840
atctgccgcc gcgatcgcca ccatggcctt accagtgacc gccttgctcc tgccgctggc    3900
cttgctgctc cacgccgcca ggccggacat cgtgatgacc cagtctcctt ccaccctgtc    3960
tgcgtctgtc ggagacagag tcaccatcac ttgccgggcc agtcagggtg tctatcagtg    4020
gttggcctgg tatcagcaga agccaggaa agcccctaac ctcctgatct ataaggcgtc    4080
tcatttatac aatggggtcc catcaagatt cagtggcagt ggctccggga cagacttcac    4140
tctcaccatc agcagcctgc agcctgatga ttttgcgact tattactgcc aacagcttaa    4200
tagttacccg ctcactttcg gcggagggac caaggtggaa atcaaacgtg gcggtggctc    4260
tggaggtggt tccggcggtg gctctggcgg tggctctcag gtacagctgc agcagtcagg    4320
ggctgaggtg aagaagcctg gtcctcggt gaaggtctcc tgcaagactt ctggatacac    4380
```

```
cttcaccggc tactatatgc actgggtgcg gcaggcccct ggacaagggt ttgagtggat   4440
gggatggatc gaccctaaca gtggtgccac aacctatgca cagaaatttc agggcaggct   4500
catcctgagc cgggacacgt ccatcaacac agcctacatg gaactgagga ggctgacatc   4560
tgatgacacg gctgtatatt actgtgcaaa aaagacaact cagactacgt gggggttttcc  4620 tttttggggc aagggaccac cggtcaccgt ctcgagtacg cgtgccctga gcaactccat   4680
catgtacttc agccacttcg tgccggtctt cctgccagcg aagcccacca cgacgccagc   4740
gccgcgacca ccaacaccgg cgcccaccat cgcgtcgcag ccctgtccc tgcgcccaga    4800 ggcgtgccgg ccagcggcgg ggggcgcagt gcacacgagg gggctggact cgcctgtga   4860 tatctacatc tgggcgccct tggccgggac ttgtggggtc cttctcctgt cactggttat   4920
caccaaacgg ggcagaaaga aactcctgta tatattcaaa caaccattta tgagaccagt   4980
acaaactact caagaggaag atggctgtag ctgccgattt ccagaagaag aagaaggagg   5040
atgtgaactg agagtgaagt tcagcaggag cgcagacgcc cccgcgtacc agcagggcca   5100
gaaccagctc tataacgagc tcaatctagg acgaagagag gagtacgatg tttttggacaa  5160 gagacgtggc cgggaccctg agatggggg aaagccgaga aggaagaacc ctcaggaagg    5220
cctgtacaat gaactgcaga agataagat ggcggaggcc tacagtgaga ttgggatgaa    5280
aggcgagcgc cggaggggca aggggcacga tggcctttac cagggtctca gtacagccac   5340
caaggacacc tacgacgccc ttcacatgca ggccctgccc cctcgctaaa tgcattctag    5400
agcggccgct cgagcagaaa ctcatctcag aagaggatct ggcagcaaat gatatcctgg    5460
attacaagga tgacgacgat aaggtttaaa cgggccggcc gcggtctgta caagtaggat    5520
tcgtcgaggg acctaataac ttcgtatagc atacattata cgaagttata catgtttaag    5580
ggttccggtt ccactaggta caattcgata tcaagcttat cgataatcaa cctctggatt    5640
acaaaatttg tgaaagattg actggtattc ttaactatgt tgctcctttt acgctatgtg   5700
gatacgctgc tttaatgcct ttgtatcatg ctattgcttc ccgtatggct ttcattttct   5760
cctccttgta taaatcctgg ttgctgtctc tttatgagga gttgtggccc gttgtcaggc   5820
aacgtggcgt ggtgtgcact gtgtttgctg acgcaacccc cactggttgg ggcattgcca   5880
ccacctgtca gctcctttcc gggactttcg cttttccccct ccctattgcc acggcggaac   5940
tcatcgccgc ctgccttgcc cgctgctgga caggggctcg gctgttgggc actgacaatt   6000
ccgtggtgtt gtcggggaaa tcatcgtcct ttccttggct gctcgcctgt gttgccacct   6060
ggattctgcg cgggacgtcc ttctgctacg tcccttcggc cctcaatcca gcggaccttc   6120
cttcccgcgg cctgctgccg gctctgcggc ctcttccgcg tcttcgcctt cgccctcaga   6180
cgagtcggat ctccctttgg gccgcctccc cgcatcgata ccgtcgacct cgatcgagac   6240
ctagaaaaac atggagcaat cacaagtagc aatacagcag ctaccaatgc tgattgtgcc   6300
tggctagaag cacaagagga ggaggaggtg gttttccag tcacacctca ggtacccttta    6360 agaccaatga cttacaaggc agctgtagat cttagccact tttaaaga aaggggggga     6420 ctggaagggc taattcactc ccaacgaaga caagatatcc ttgatctgtg gatctaccac   6480
acacaaggct acttccctga ttggcagaac tacacaccag ggccagggat cagatatcca   6540
ctgacctttg gatggtgcta caagctagta ccagttgagc aagagaaggt agaagaagcc   6600
aatgaaggag agaacacccg cttgttacac cctgtgagcc tgcatgggat ggatgacccg   6660
gagagagaag tattagagtg gaggtttgac agccgcctag catttcatca catggcccga   6720
```

```
gagctgcatc cggactgtac tgggtctctc tggttagacc agatctgagc ctgggagctc    6780
tctggctaac tagggaaccc actgcttaag cctcaataaa gcttgccttg agtgcttcaa    6840
gtagtgtgtg cccgtctgtt gtgtgactct ggtaactaga gatccctcag acccttttag    6900
tcagtgtgga aaatctctag cagcatgtga gcaaaaggcc agcaaaaggc caggaaccgt    6960
aaaaaggccg cgttgctggc gtttttccat aggctccgcc cccctgacga gcatcacaaa    7020
aatcgacgct caagtcagag gtggcgaaac ccgacaggac tataaagata ccaggcgttt    7080
ccccctggaa gctccctcgt gcgctctcct gttccgaccc tgccgcttac cggatacctg    7140
tccgcctttc tcccttcggg aagcgtggcg ctttctcata gctcacgctg taggtatctc    7200
agttcggtgt aggtcgttcg ctccaagctg ggctgtgtgc acgaaccccc cgttcagccc    7260
gaccgctgcg ccttatccgg taactatcgt cttgagtcca acccggtaag acacgactta    7320
tcgccactgg cagcagccac tggtaacagg attagcagag cgaggtatgt aggcggtgct    7380
acagagttct tgaagtggtg gcctaactac ggctacacta agaacagta tttggtatc     7440 tgcgctctgc tgaagccagt taccttcgga aaaagagttg gtagctcttg atccggcaaa    7500
caaaccaccg ctggtagcgg tggttttttt gtttgcaagc agcagattac gcgcagaaaa    7560
aaaggatctc aagaagatcc tttgatcttt tctacggggt ctgacgctca gtggaacgaa    7620
aactcacgtt aagggatttt ggtcatgaga ttatcaaaaa ggatcttcac ctagatcctt    7680
ttaaattaaa aatgaagttt taaatcaatc taaagtatat atgagtaaac ttggtctgac    7740
agttaccaat gcttaatcag tgaggcacct atctcagcga tctgtctatt tcgttcatcc    7800
atagttgcct gactccccgt cgtgtagata actacgatac ggggggcttt accatctggc    7860
cccagtgctg caatgatacc gcgagaccca cgctcaccgg ctccagattt atcagcaata    7920
aaccagccag ccggaagggc cgagcgcaga agtggtcctg caactttatc cgcctccatc    7980
cagtctatta attgttgccg ggaagctaga gtaagtagtt cgccagttaa tagtttgcgc    8040
aacgttgttg ccattgctac aggcatcgtg gtgtcacgct cgtcgtttgg tatggcttca    8100
ttcagctccg gttcccaacg atcaaggcga gttacatgat cccccatgtt gtgcaaaaaa    8160
gcggttagct ccttcggtcc tccgatcgtt gtcagaagta agttggccgc agtgttatca    8220
ctcatggtta tggcagcact gcataattct cttactgtca tgccatccgt aagatgcttt    8280
tctgtgactg gtgagtactc aaccaagtca ttctgagaat agtgtatgcg gcgaccgagt    8340
tgctcttgcc cggcgtcaat acgggataat accgcgccac atagcagaac tttaaaagtg    8400
ctcatcattg gaaaacgttc ttcggggcga aaactctcaa ggatcttacc gctgttgaga    8460
tccagttcga tgtaacccac tcgtgcaccc aactgatctt cagcatcttt tactttcacc    8520
agcgtttctg ggtgagcaaa aacaggaagg caaaatgccg caaaaaaggg aataagggcg    8580
acacggaaat gttgaatact catactcttc ctttttcaat attattgaag catttatcag    8640
ggttattgtc tcatgagcgg atacatattt gaatgtattt agaaaaataa acaaataggg    8700
gtcccgcgca catttccccg aaaagtgcca cctgac                             8736
```

<210> SEQ ID NO 10
<211> LENGTH: 63
<212> TYPE: DNA
<213> ORGANISM: Artificial Sequence
<220> FEATURE:
<223> OTHER INFORMATION: coding sequence

<400> SEQUENCE: 10

```
atctacatct gggcgcccct tggccgggac tgtggggtcc ttctcctgtc actggttatc    60
```

```
acc                                                                63
```

<210> SEQ ID NO 11
<211> LENGTH: 261
<212> TYPE: DNA
<213> ORGANISM: Artificial Sequence
<220> FEATURE:
<223> OTHER INFORMATION: coding sequence

<400> SEQUENCE: 11

```
gccctgagca actccatcat gtacttcagc cacttcgtgc cggtcttcct gccagcgaag    60
cccaccacga cgccagcgcc gcgaccacca acaccggcgc ccaccatcgc gtcgcagccc   120
ctgtccctgc gcccagaggc gtgccggcca gcggcggggg gcgcagtgca cacgaggggg   180
ctggacttcg cctgtgatat ctacatctgg gcgcccttgg ccgggacttg tggggtcctt   240
ctcctgtcac tggttatcac c                                            261
```

<210> SEQ ID NO 12
<211> LENGTH: 126
<212> TYPE: DNA
<213> ORGANISM: Artificial Sequence
<220> FEATURE:
<223> OTHER INFORMATION: coding sequence

<400> SEQUENCE: 12

```
aaacggggca gaaagaaact cctgtatata ttcaaacaac catttatgag accagtacaa    60
actactcaag aggaagatgg ctgtagctgc cgatttccag aagaagaaga aggaggatgt   120
gaactg                                                             126
```

<210> SEQ ID NO 13
<211> LENGTH: 336
<212> TYPE: DNA
<213> ORGANISM: Artificial Sequence
<220> FEATURE:
<223> OTHER INFORMATION: coding sequence

<400> SEQUENCE: 13

```
agagtgaagt tcagcaggag cgcagacgcc cccgcgtacc agcagggcca gaaccagctc    60
tataacgagc tcaatctagg acgaagagag gagtacgatg ttttggacaa gagacgtggc   120
cgggaccctg agatggggg aaagccgaga aggaagaacc ctcaggaagg cctgtacaat    180
gaactgcaga agataagat ggcggaggcc tacagtgaga ttgggatgaa aggcgagcgc    240
cggaggggca aggggcacga tggcctttac cagggtctca gtacagccac caaggacacc   300
tacgacgccc ttcacatgca ggccctgccc cctcgc                            336
```

<210> SEQ ID NO 14
<211> LENGTH: 4
<212> TYPE: PRT
<213> ORGANISM: Artificial Sequence
<220> FEATURE:
<223> OTHER INFORMATION: spacer

<400> SEQUENCE: 14

Gly Gly Ser Gly
1

<210> SEQ ID NO 15
<211> LENGTH: 8
<212> TYPE: PRT
<213> ORGANISM: Artificial Sequence

```
<220> FEATURE:
<223> OTHER INFORMATION: spacer

<400> SEQUENCE: 15

Gly Ser Gly Ser Gly Ser Gly Ser
1               5

<210> SEQ ID NO 16
<211> LENGTH: 10
<212> TYPE: PRT
<213> ORGANISM: Artificial Sequence
<220> FEATURE:
<223> OTHER INFORMATION: spacer

<400> SEQUENCE: 16

Gly Gly Gly Ser Ser Gly Gly Gly Ser Gly
1               5                   10

<210> SEQ ID NO 17
<211> LENGTH: 5
<212> TYPE: PRT
<213> ORGANISM: Artificial Sequence
<220> FEATURE:
<223> OTHER INFORMATION: spacer

<400> SEQUENCE: 17

Gly Gly Cys Gly Gly
1               5

<210> SEQ ID NO 18
<211> LENGTH: 21
<212> TYPE: PRT
<213> ORGANISM: Artificial Sequence
<220> FEATURE:
<223> OTHER INFORMATION: signal peptide

<400> SEQUENCE: 18

Met Ala Leu Pro Val Thr Ala Leu Leu Leu Pro Leu Ala Leu Leu Leu
1               5                   10                  15

His Ala Ala Arg Pro
            20

<210> SEQ ID NO 19
<211> LENGTH: 485
<212> TYPE: PRT
<213> ORGANISM: Artificial Sequence
<220> FEATURE:
<223> OTHER INFORMATION: fusion protein

<400> SEQUENCE: 19

Asp Ile Val Met Thr Gln Ser Pro Ser Thr Leu Ser Ala Ser Val Gly
1               5                   10                  15

Asp Arg Val Thr Ile Thr Cys Arg Ala Ser Gln Gly Val Tyr Gln Trp
            20                  25                  30

Leu Ala Trp Tyr Gln Gln Lys Pro Gly Lys Ala Pro Asn Leu Leu Ile
        35                  40                  45

Tyr Lys Ala Ser His Leu Tyr Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Leu Asn Ser Tyr Pro Leu
                85                  90                  95

Thr Phe Gly Gly Gly Thr Lys Val Glu Ile Lys Arg Gly Gly Gly Ser
```

```
            100                 105                 110
Gly Gly Gly Ser Gly Gly Gly Ser Gly Gly Gly Ser Gln Val Gln Leu
            115                 120                 125
Gln Gln Ser Gly Ala Glu Val Lys Lys Pro Gly Ser Ser Val Lys Val
            130                 135                 140
Ser Cys Lys Thr Ser Gly Tyr Thr Phe Thr Gly Tyr Tyr Met His Trp
145                 150                 155                 160
Val Arg Gln Ala Pro Gly Gln Gly Phe Glu Trp Met Gly Trp Ile Asp
                165                 170                 175
Pro Asn Ser Gly Ala Thr Thr Tyr Ala Gln Lys Phe Gln Gly Arg Leu
                180                 185                 190
Ile Leu Ser Arg Asp Thr Ser Ile Asn Thr Ala Tyr Met Glu Leu Arg
                195                 200                 205
Arg Leu Thr Ser Asp Asp Thr Ala Val Tyr Tyr Cys Ala Lys Lys Thr
            210                 215                 220
Thr Gln Thr Thr Trp Gly Phe Pro Phe Trp Gly Gln Gly Thr Thr Val
225                 230                 235                 240
Thr Val Ser Ser Ala Leu Ser Asn Ser Ile Met Tyr Phe Ser His Phe
                245                 250                 255
Val Pro Val Phe Leu Pro Ala Lys Pro Thr Thr Thr Pro Ala Pro Arg
                260                 265                 270
Pro Pro Thr Pro Ala Pro Thr Ile Ala Ser Gln Pro Leu Ser Leu Arg
                275                 280                 285
Pro Glu Ala Cys Arg Pro Ala Ala Gly Gly Ala Val His Thr Arg Gly
            290                 295                 300
Leu Asp Phe Ala Cys Asp Ile Tyr Ile Trp Ala Pro Leu Ala Gly Thr
305                 310                 315                 320
Cys Gly Val Leu Leu Leu Ser Leu Val Ile Thr Lys Arg Gly Arg Lys
                325                 330                 335
Lys Leu Leu Tyr Ile Phe Lys Gln Pro Phe Met Arg Pro Val Gln Thr
                340                 345                 350
Thr Gln Glu Glu Asp Gly Cys Ser Cys Arg Phe Pro Glu Glu Glu Glu
            355                 360                 365
Gly Gly Cys Glu Leu Arg Val Lys Phe Ser Arg Ser Ala Asp Ala Pro
            370                 375                 380
Ala Tyr Gln Gln Gly Gln Asn Gln Leu Tyr Asn Glu Leu Asn Leu Gly
385                 390                 395                 400
Arg Arg Glu Glu Tyr Asp Val Leu Asp Lys Arg Arg Gly Arg Asp Pro
                405                 410                 415
Glu Met Gly Gly Lys Pro Arg Arg Lys Asn Pro Gln Glu Gly Leu Tyr
            420                 425                 430
Asn Glu Leu Gln Lys Asp Lys Met Ala Glu Ala Tyr Ser Glu Ile Gly
            435                 440                 445
Met Lys Gly Glu Arg Arg Arg Gly Lys Gly His Asp Gly Leu Tyr Gln
            450                 455                 460
Gly Leu Ser Thr Ala Thr Lys Asp Thr Tyr Asp Ala Leu His Met Gln
465                 470                 475                 480
Ala Leu Pro Pro Arg
                485

<210> SEQ ID NO 20
<211> LENGTH: 1455
<212> TYPE: DNA
<213> ORGANISM: Artificial Sequence
```

<220> FEATURE:
<223> OTHER INFORMATION: fusion gene

<400> SEQUENCE: 20

```
gacatcgtga tgacccagtc tccttccacc ctgtctgcgt ctgtcggaga cagagtcacc      60
atcacttgcc gggccagtca gggtgtctat cagtggttgg cctggtatca gcagaagcca     120
gggaaagccc ctaacctcct gatctataag gcgtctcatt tatacaatgg ggtcccatca     180
agattcagtg gcagtggctc cgggacagac ttcactctca ccatcagcag cctgcagcct     240
gatgattttg cgacttatta ctgccaacag cttaatagtt acccgctcac tttcggcgga     300
gggaccaagg tggaaatcaa acgtggcggt ggctctggag tggttccgg cggtggctct     360
ggcggtggct ctcaggtaca gctgcagcag tcaggggctg aggtgaagaa gcctgggtcc     420
tcggtgaagg tctcctgcaa gacttctgga tacaccttca ccggctacta tatgcactgg     480
gtgcggcagg cccctggaca agggtttgag tggatgggat ggatcgaccc taacagtggt     540
gccacaacct atgcacagaa atttcagggc aggctcatcc tgagccggga cacgtccatc     600
aacacagcct acatggaact gaggaggctg acatctgatg acacggctgt atattactgt     660
gcaaaaaaga caactcagac tacgtggggg tttccttttt ggggccaagg gaccacggtc     720
accgtctcga gtgccctgag caactccatc atgtacttca gccacttcgt gccggtcttc     780
ctgccagcga agcccaccac gacgccagcg ccgcgaccac caacaccggc gcccaccatc     840
gcgtcgcagc ccctgtccct gcgcccagag gcgtgccggc cagcggcggg gggcgcagtg     900
cacacgaggg ggctggactt cgcctgtgat atctacatct gggcgccctt ggccgggact     960
tgtgggtcc ttctcctgtc actggttatc accaaacggg gcagaaagaa actcctgtat    1020
atattcaaac aaccatttat gagaccagta caaactactc aagaggaaga tggctgtagc    1080
tgccgatttc cagaagaaga agaaggagga tgtgaactga gagtgaagtt cagcaggagc    1140
gcagacgccc ccgcgtacca gcagggccag aaccagctct ataacgagct caatctagga    1200
cgaagagagg agtacgatgt tttggacaag agacgtggcc gggaccctga tggggggga    1260
aagccgagaa ggaagaaccc tcaggaaggc ctgtacaatg aactgcagaa agataagatg    1320
gcggaggcct acagtgagat tgggatgaaa ggcgagcgcc ggaggggcaa ggggcacgat    1380
ggcctttacc agggtctcag tacagccacc aaggacacct cgacgccct tcacatgcag    1440
gccctgcccc ctcgc                                                    1455
```

<210> SEQ ID NO 21
<211> LENGTH: 1518
<212> TYPE: DNA
<213> ORGANISM: Artificial Sequence
<220> FEATURE:
<223> OTHER INFORMATION: fusion gene with signal peptide

<400> SEQUENCE: 21

```
atggccttac cagtgaccgc cttgctcctg ccgctggcct tgctgctcca cgccgccagg      60
ccggacatcg tgatgaccca gtctccttcc accctgtctg cgtctgtcgg agacagagtc     120
accatcactt gccgggccag tcagggtgtc tatcagtggt tggcctggta tcagcagaag     180
ccagggaaag cccctaacct cctgatctat aaggcgtctc atttatacaa tggggtccca     240
tcaagattca gtggcagtgg ctccgggaca gacttcactc tcaccatcag cagcctgcag     300
cctgatgatt ttgcgactta ttactgccaa cagcttaata gttacccgct cactttcggc     360
ggagggacca aggtggaaat caaacgtggc ggtggctctg gaggtggttc cggcggtggc     420
```

```
tctggcggtg gctctcaggt acagctgcag cagtcagggg ctgaggtgaa gaagcctggg    480
tcctcggtga aggtctcctg caagacttct ggatacacct tcaccggcta ctatatgcac    540
tgggtgcggc aggcccctgg acaagggttt gagtggatgg gatggatcga ccctaacagt    600
ggtgccacaa cctatgcaca gaaatttcag ggcaggctca tcctgagccg ggacacgtcc    660
atcaacacag cctacatgga actgaggagg ctgacatctg atgacacggc tgtatattac    720
tgtgcaaaaa agacaactca gactacgtgg gggtttcctt ttggggcca agggaccacg    780
gtcaccgtct cgagtgccct gagcaactcc atcatgtact cagccactt cgtgccggtc    840
ttcctgccag cgaagcccac cacgacgcca gcgccgcgac caccaacacc ggcgcccacc    900
atcgcgtcgc agcccctgtc cctgcgccca gaggcgtgcc ggccagcggc gggggggcgca   960
gtgcacacga gggggctgga cttcgcctgt gatatctaca tctgggcgcc cttggccggg   1020
acttgtgggg tccttctcct gtcactggtt atcaccaaac ggggcagaaa gaaactcctg   1080
tatatattca acaaccatt tatgagacca gtacaaacta ctcaagagga agatggctgt   1140
agctgccgat ttccagaaga agaagaagga ggatgtgaac tgagagtgaa gttcagcagg   1200
agcgcagacg cccccgcgta ccagcagggc cagaaccagc tctataacga gctcaatcta   1260
ggacgaagag aggagtacga tgttttggac aagagacgtg gccgggaccc tgagatgggg   1320
ggaaagccga aaggaagaa ccctcaggaa ggcctgtaca atgaactgca gaaagataag   1380
atggcggagg cctacagtga gattgggatg aaaggcgagc gccggagggg caaggggcac   1440
gatggccttt accagggtct cagtacagcc accaaggaca cctacgacgc ccttcacatg   1500
caggcccctgc cccctcgc                                               1518
```

<210> SEQ ID NO 22
<211> LENGTH: 506
<212> TYPE: PRT
<213> ORGANISM: Artificial Sequence
<220> FEATURE:
<223> OTHER INFORMATION: fusion protein with signal peptide

<400> SEQUENCE: 22

```
Met Ala Leu Pro Val Thr Ala Leu Leu Leu Pro Leu Ala Leu Leu Leu
1               5                   10                  15

His Ala Ala Arg Pro Asp Ile Val Met Thr Gln Ser Pro Ser Thr Leu
                20                  25                  30

Ser Ala Ser Val Gly Asp Arg Val Thr Ile Thr Cys Arg Ala Ser Gln
            35                  40                  45

Gly Val Tyr Gln Trp Leu Ala Trp Tyr Gln Gln Lys Pro Gly Lys Ala
        50                  55                  60

Pro Asn Leu Leu Ile Tyr Lys Ala Ser His Leu Tyr Asn Gly Val Pro
65                  70                  75                  80

Ser Arg Phe Ser Gly Ser Gly Ser Gly Thr Asp Phe Thr Leu Thr Ile
                85                  90                  95

Ser Ser Leu Gln Pro Asp Asp Phe Ala Thr Tyr Tyr Cys Gln Gln Leu
                100                 105                 110

Asn Ser Tyr Pro Leu Thr Phe Gly Gly Gly Thr Lys Val Glu Ile Lys
            115                 120                 125

Arg Gly Gly Gly Ser Gly Gly Gly Ser Gly Gly Ser Gly Gly Gly
        130                 135                 140

Ser Gln Val Gln Leu Gln Gln Ser Gly Ala Glu Val Lys Lys Pro Gly
145                 150                 155                 160

Ser Ser Val Lys Val Ser Cys Lys Thr Ser Gly Tyr Thr Phe Thr Gly
```

```
                165                 170                 175
Tyr Tyr Met His Trp Val Arg Gln Ala Pro Gly Gln Gly Phe Glu Trp
            180                 185                 190

Met Gly Trp Ile Asp Pro Asn Ser Gly Ala Thr Thr Tyr Ala Gln Lys
        195                 200                 205

Phe Gln Gly Arg Leu Ile Leu Ser Arg Asp Thr Ser Ile Asn Thr Ala
    210                 215                 220

Tyr Met Glu Leu Arg Arg Leu Thr Ser Asp Asp Thr Ala Val Tyr Tyr
225                 230                 235                 240

Cys Ala Lys Lys Thr Thr Gln Thr Thr Trp Gly Phe Pro Phe Trp Gly
                245                 250                 255

Gln Gly Thr Thr Val Thr Val Ser Ser Ala Leu Ser Asn Ser Ile Met
            260                 265                 270

Tyr Phe Ser His Phe Val Pro Val Phe Leu Pro Ala Lys Pro Thr Thr
        275                 280                 285

Thr Pro Ala Pro Arg Pro Pro Thr Pro Ala Pro Thr Ile Ala Ser Gln
    290                 295                 300

Pro Leu Ser Leu Arg Pro Glu Ala Cys Arg Pro Ala Ala Gly Gly Ala
305                 310                 315                 320

Val His Thr Arg Gly Leu Asp Phe Ala Cys Asp Ile Tyr Ile Trp Ala
                325                 330                 335

Pro Leu Ala Gly Thr Cys Gly Val Leu Leu Leu Ser Leu Val Ile Thr
            340                 345                 350

Lys Arg Gly Arg Lys Lys Leu Leu Tyr Ile Phe Lys Gln Pro Phe Met
        355                 360                 365

Arg Pro Val Gln Thr Thr Gln Glu Glu Asp Gly Cys Ser Cys Arg Phe
    370                 375                 380

Pro Glu Glu Glu Glu Gly Gly Cys Glu Leu Arg Val Lys Phe Ser Arg
385                 390                 395                 400

Ser Ala Asp Ala Pro Ala Tyr Gln Gln Gly Gln Asn Gln Leu Tyr Asn
                405                 410                 415

Glu Leu Asn Leu Gly Arg Arg Glu Glu Tyr Asp Val Leu Asp Lys Arg
            420                 425                 430

Arg Gly Arg Asp Pro Glu Met Gly Gly Lys Pro Arg Arg Lys Asn Pro
        435                 440                 445

Gln Glu Gly Leu Tyr Asn Glu Leu Gln Lys Asp Lys Met Ala Glu Ala
    450                 455                 460

Tyr Ser Glu Ile Gly Met Lys Gly Glu Arg Arg Arg Gly Lys Gly His
465                 470                 475                 480

Asp Gly Leu Tyr Gln Gly Leu Ser Thr Ala Thr Lys Asp Thr Tyr Asp
                485                 490                 495

Ala Leu His Met Gln Ala Leu Pro Pro Arg
            500                 505

<210> SEQ ID NO 23
<211> LENGTH: 756
<212> TYPE: DNA
<213> ORGANISM: Artificial Sequence
<220> FEATURE:
<223> OTHER INFORMATION: Ki-3 scFV

<400> SEQUENCE: 23
gacattgtgc tcacccagtc tccatcctcc ctggctatgt cagtaggaca gaaggtcgct      60
atgaactgca agtccagtca gagcctttta aatagtaatg atcaaaagaa ctatttggcc    120
```

```
tggtaccagc agaaacctga acagtctcct aaacttctgg tatactttgc atccactggg      180
ggatctgggg tacctgatcg cttcgtaggc agtggatctg ggacagattt cactcttacc      240
atcagcagtg tgcaggctga agacctggca gattacttct gtcagcaaca ttatagcact      300
ccgtacacgt tcggagggg gaccaagctg gagctgaaac gggcggcgg tggctctgga       360 ggtggttccg gcggtggctc tggcggtggc tctcaggtgc agctgcagca gtctgggcct      420
gacctggtga agcctgggc ttcagtgagg atctcctgca aggcttctgg ctacaccttc       480
acaacctact atatccactg ggtgaagcag aggcctggac agggacttga gtggattgga      540
tggatttatc ctggaaatgg tattgctaag tacaatgaga gtttaagggg caaggccaca      600
ctgagttcag acacatcttc caacacagcc tacatgcagc tcagcagcct gacctctgag      660
gactctgcgg tctatttctg tgcaagagct tattactacg gtactagaga tgctatggac      720 cattgggggcc aagggaccac ggtcaccgtc tcctca                               756

<210> SEQ ID NO 24
<211> LENGTH: 765
<212> TYPE: DNA
<213> ORGANISM: Artificial Sequence
<220> FEATURE:
<223> OTHER INFORMATION: anti-CD30 scFV

<400> SEQUENCE: 24
tcgacgaaca ttgtaatgac ccaatctccc agatccatgt ccatgtctgt aggagagagg       60
gtcaccttga gctgcaaggc cagtgagaat gtggatactt atgtatcctg gtatcaacag      120
aaaccagagc agtctcctaa actcctgata tacgggcat ccaaccggta cactggggtc       180
cccgatcgct tcacaggcag tggatctgca acagatttca ctctgaccat cagcagtgtg      240
caggctgaag accttgcaga ttatcactgt ggacagagtt acagatatcc tcccacgttc      300 ggaggggga ccaagctgga ataaaaggg ggcggtggct ctggaggtgg ttccggcggt        360
ggctctggcg gtggctctag atctcaggtc cagcttcacg agtctggggc tgaagtggca      420
aaacctgggg cctcagtgaa gatgtcctgc aaggcttctg gctacacctt tactacctac      480
tggatgcact ggataaaaca gaggcctgga cagggtctgg aatggattgg atacattaat      540
cctagcactg gttatactga ctacaatcag aacttcaagg acaaggccac attgactgca      600
gacaaatcct ccagaacagc ctacatgcaa ctgagcagcc tgacatctga ggactctaca      660
gtctattact gtacaagaag gggaccctcg tatggtaacc acggggcctg gtttccttac      720
tggggccaag gactctggt cactgtctct gcagtctcga gcggt                       765

<210> SEQ ID NO 25
<211> LENGTH: 732
<212> TYPE: DNA
<213> ORGANISM: Artificial Sequence
<220> FEATURE:
<223> OTHER INFORMATION: AK30 scFV

<400> SEQUENCE: 25
gacatcgtga tgacccagtc tccttccacc ctgtctgcgt ctgtcggaga cagagtcacc       60
atcacttgcc gggccagtca gggtgtctat cagtggttgg cctggtatca gcagaagcca      120
gggaaagccc ctaacctcct gatctataag gcgtctcatt tatacaatgg ggtcccatca      180
agattcagtg gcagtggctc cgggacagac ttcactctca ccatcagcag cctgcagcct      240
gatgattttg cgacttatta ctgccaacag cttaatagtt acccgctcac tttcggcgga      300
gggaccaagg tggaaatcaa acgtggcggt ggctctggag gtggttccgg cggtggctct      360
```

```
ggcggtggct ctcaggtaca gctgcagcag tcaggggctg aggtgaagaa gcctgggtcc    420
tcggtgaagg tctcctgcaa gacttctgga tacaccttca ccggctacta tatgcactgg    480
gtgcggcagg cccctggaca agggtttgag tggatgggat ggatcgaccc taacagtggt    540
gccacaacct atgcacagaa atttcagggc aggctcatcc tgagccggga cacgtccatc    600
aacacagcct acatggaact gaggaggctg acatctgatg acacggctgt atattactgt    660
gcaaaaaaga caactcagac tacgtggggg tttccttttt ggggccaagg accacggtc    720 accgtctcga gt                                                         732

<210> SEQ ID NO 26
<211> LENGTH: 63
<212> TYPE: DNA
<213> ORGANISM: Artificial Sequence
<220> FEATURE:
<223> OTHER INFORMATION: signal peptide coding sequence

<400> SEQUENCE: 26
atggccttac cagtgaccgc cttgctcctg ccgctggcct tgctgctcca cgccgccagg    60
ccg                                                                  63

<210> SEQ ID NO 27
<211> LENGTH: 1785
<212> TYPE: DNA
<213> ORGANISM: Homo sapiens

<400> SEQUENCE: 27
atgcgcgtcc tcctcgccgc gctgggactg ctgttcctgg gggcgctacg agccttccca    60
caggatcgac ccttcgagga cacctgtcat ggaaacccca gccactacta tgacaaggct    120
gtcaggaggt gctgttaccg ctgccccatg gggctgttcc gacacagca gtgcccacag    180 aggcctactg actgcaggaa gcagtgtgag cctgactact acctggatga ggccgaccgc    240
tgtacagcct gcgtgacttg ttctcgagac gacctcgtgg agaagacgcc gtgtgcatgg    300
aactcctccc gtgtctgcga atgtcgaccc ggcatgttct gttccacgtc tgccgtcaac    360
tcctgtgccc gctgcttctt ccattctgtc tgtccggcag ggatgattgt caagttccca    420
ggcacggcgc agaagaacac ggtctgtgag ccggcttccc caggggtcag ccctgcctgt    480
gccagcccag agaactgcaa ggaaccctcc agtggcacca tccccaggc caagcccacc    540 ccggtgtccc cagcaacctc cagtgccagc accatgcctg taagagggg cacccgcctc    600 gcccaggaag ctgcttctaa actgacgagg gctcccgact ctccctcctc tgtgggaagg    660
cctagttcag atccaggtct gtccccaaca cagccatgcc cagaggggtc tggtgattgc    720
agaaagcagt gtgagcccga ctactacctg gacgaggccg gccgctgcac ggcctgcgtg    780
agctgttctc gagatgacct tgtggagaag acgccatgtg catggaactc ctcccgcacc    840
tgcgaatgtc gacctggcat gatctgtgcc acatcagcca ccaactcctg tgcccgctgt    900 gtccctacc caatctgtgc agcagagacg gtcaccaagc cccaggatat ggctgagaag    960
gacaccacct tgaggcgcc accctgggg acccagccgg actgcaaccc caccccagag    1020
aatggcgagc gcctgccag caccagcccc actcagagct gctgtgga ctcccaggcc    1080 agtaagacgc tgcccatccc aaccagcgct cccgtcgctc tctcctccac ggggaagccc    1140
gttctggatg cagggccagt gctcttctgg gtgatcctgg tgttggttgt ggtggtcggc    1200
tccagcgcct tcctcctgtg ccaccggagg gcctgcagga agcgaattcg gcagaagctc    1260
```

-continued

| | |
|---|---|
| cacctgtgct acccggtcca gacctcccag cccaagctag agcttgtgga ttccagaccc | 1320 |
| aggaggagct caacgcagct gaggagtggt gcgtcggtga cagaacccgt cgcggaagag | 1380 |
| cgagggttaa tgagccagcc actgatggag acctgccaca gcgtgggggc agcctacctg | 1440 |
| gagagcctgc cgctgcagga tgccagcccg gccgggggcc cctcgtcccc cagggacctt | 1500 |
| cctgagcccc gggtgtccac ggagcacacc aataacaaga ttgagaaaat ctacatcatg | 1560 |
| aaggctgaca ccgtgatcgt ggggaccgtg aaggctgagc tgccggaggg ccggggcctg | 1620 |
| gcggggccag cagagcccga gttggaggag gagctggagg cggaccatac cccccactac | 1680 |
| cccgagcagg agacagaacc gcctctgggc agctgcagcg atgtcatgct ctcagtggaa | 1740 |
| gaggaaggga aagaagaccc cttgcccaca gctgcctctg gaaag | 1785 |

<210> SEQ ID NO 28
<211> LENGTH: 57
<212> TYPE: DNA
<213> ORGANISM: Artificial Sequence
<220> FEATURE:
<223> OTHER INFORMATION: P2A

<400> SEQUENCE: 28

| | |
|---|---|
| gctactaact tcagcctgct gaagcaggct ggagacgtgg aggagaaccc tggacct | 57 |

<210> SEQ ID NO 29
<211> LENGTH: 513
<212> TYPE: DNA
<213> ORGANISM: Artificial Sequence
<220> FEATURE:
<223> OTHER INFORMATION: luciferase

<400> SEQUENCE: 29

| | |
|---|---|
| atggtcttca cactcgaaga tttcgttggg gactggcgac agacagccgg ctacaacctg | 60 |
| gaccaagtcc ttgaacaggg aggtgtgtcc agtttgtttc agaatctcgg ggtgtccgta | 120 |
| actccgatcc aaaggattgt cctgagcggt gaaaatgggc tgaagatcga catccatgtc | 180 |
| atcatcccgt atgaaggtct gagcggcgac caaatgggcc agatcgaaaa aatttttaag | 240 |
| gtggtgtacc ctgtggatga tcatcacttt aaggtgatcc tgcactatgg cacactggta | 300 |
| atcgacgggg ttacgccgaa catgatcgac tatttcggac ggccgtatga aggcatcgcc | 360 |
| gtgttcgacg gcaaaaagat cactgtaaca gggaccctgt ggaacggcaa caaaattatc | 420 |
| gacgagcgcc tgatcaaccc cgacggctcc ctgctgttcc gagtaaccat caacggagtg | 480 |
| accggctggc ggctgtgcga acgcattctg gcg | 513 |

<210> SEQ ID NO 30
<211> LENGTH: 3692
<212> TYPE: DNA
<213> ORGANISM: Artificial Sequence
<220> FEATURE:
<223> OTHER INFORMATION: CD30-P2A-Nanoluc? Luciferase

<400> SEQUENCE: 30

| | |
|---|---|
| atggtcttca cactcgaaga tttcgttggg gactggcgac agacagccgg ctacaacctg | 60 |
| gaccaagtcc ttgaacaggg aggtgtgtcc agtttgtttc agaatctcgg ggtgtccgta | 120 |
| actccgatcc aaaggattgt cctgagcggt gaaaatgggc tgaagatcga catccatgtc | 180 |
| atcatcccgt atgaaggtct gagcggcgac caaatgggcc agatcgaaaa aatttttaag | 240 |
| gtggtgtacc ctgtggatga tcatcacttt aaggtgatcc tgcactatgg cacactggta | 300 |
| atcgacgggg ttacgccgaa catgatcgac tatttcggac ggccgtatga aggcatcgcc | 360 |

```
gtgttcgacg gcaaaaagat cactgtaaca gggaccctgt ggaacggcaa caaaattatc      420
gacgagcgcc tgatcaaccc cgacggctcc ctgctgttcc gagtaaccat caacggagtg      480
accggctggc ggctgtgcga acgcattctg gcggtcgagg gaagcggagc tactaacttc      540
agcctgctga agcaggctgg agacgtggag gagaaccctg gacctgtcga catgaccgag      600
tacaagccca cggtgcgcct cgccacccgc gacgacgtcc cccgggcagt acgcaccctc      660
gccgccgcgt tcgccgacta ccccgccacg cgccacaccg tcgatccaga ccgccacatc      720
gagcgggtca ccgagctgca agaactcttc ctcacgcgcg tcgggctcga catcggcaag      780
gtgtgggtcg cggacgacgg cgccgcggtg cggtctgga ccacgccgga gagcgtcgaa      840 gcggggcgg tgttcgccga gatcggcccg cgcatggccg agttgagcgg ttcccggctg      900
gccgcgcagc aacagatgga aggcctcctg gcgccgcacc ggcccaagga gcccgcgtgg      960
ttcctggcca ccgtcggcgt ctcgcccgac caccagggca agggtctggg cagcgccgtc     1020
gtgctccccg gagtggaggc ggccgagcgc gccggggtgc ccgccttcct ggagacctcc     1080
gcgccccgca acctccccctt ctacgagcgg ctcggcttca ccgtcaccgc cgacgtcgag     1140
gtgcccgaag gaccgcgcac ctggtgcatg cccgcaagc ccggtgcctg atctagacat     1200
gtccaatatg accgccatgt tgacattgat tattgactag ttattaatag taatcaatta     1260
cggggtcatt agttcatagc ccatatatgg agttccgcgt tacataactt acggtaaatg     1320
gcccgcctgg ctgaccgccc aacgaccccc gcccattgac gtcaataatg acgtatgttc     1380
ccatagtaac gccaataggg actttccatt gacgtcaatg ggtggagtat ttacggtaaa     1440
ctgcccactt ggcagtacat caagtgtatc atatgccaag tccgcccct attgacgtca     1500 atgacggtaa atggcccgcc tggcattatg cccagtacat gaccttacgg gactttccta     1560
cttggcagta catctacgta ttagtcatcg ctattaccat ggtgatgcgg ttttggcagt     1620
acaccaatgg gcgtggatag cggtttgact cacggggatt tccaagtctc cacccccattg     1680 acgtcaatgg gagtttgttt tggcaccaaa atcaacggga ctttccaaaa tgtcgtaata     1740
accccgcccc gttgacgcaa atgggcggta ggcgtgtacg gtgggaggtc tatataagca     1800
gagctcgttt agtgaaccgt cagaattttg taatacgact cactataggg cggccgggaa     1860
ttcgtcgact ggatccggta ccgaggagat ctgccgccgc gatcgccatg cgcgtcctcc     1920
tcgccgcgct gggactgctg ttcctggggg cgctacgagc cttcccacag gatcgaccct     1980
tcgaggacac ctgtcatgga aaccccagcc actactatga caaggctgtc aggaggtgct     2040
gttaccgctg cccatggggg ctgttcccga cacagcagtg cccacagagg cctactgact     2100
gcaggaagca gtgtgagcct gactactacc tggatgaggc cgaccgctgt acagcctgcg     2160
tgacttgttc tcgagacgac ctcgtggaga agacgccgtg tgcatggaac tcctcccgtg     2220
tctgcgaatg tcgacccggc atgttctgtt ccacgtctgc cgtcaactcc tgtgcccgct     2280
gcttcttcca ttctgtctgt ccggcaggga tgattgtcaa gttccaggc acggcgcaga     2340 agaacacggt ctgtgagccg gcttccccag gggtcagccc tgcctgtgcc agcccagaga     2400
actgcaagga accctccagt ggcaccatcc cccaggccaa gcccaccccg gtgtccccag     2460
caacctccag tgccagcacc atgcctgtaa aggggggcac ccgcctcgcc caggaagctg     2520 cttctaaaact gacgagggct cccgactctc cctcctctgt gggaaggcct agttcagatc     2580
caggtctgtc cccaacacag ccatgcccag aggggtctgg tgattgcaga aagcagtgtg     2640
agcccgacta ctacctggac gaggccggcc gctgcacggc ctgcgtgagc tgttctcgag     2700
```

-continued

```
atgaccttgt ggagaagacg ccatgtgcat ggaactcctc ccgcacctgc gaatgtcgac    2760
ctggcatgat ctgtgccaca tcagccacca actcctgtgc ccgctgtgtc ccctacccaa    2820
tctgtgcagc agagacggtc accaagcccc aggatatggc tgagaaggac accacctttg    2880
aggcgccacc cctggggacc cagccggact gcaaccccac cccagagaat ggcgaggcgc    2940
ctgccagcac cagccccact cagagcttgc tggtggactc ccaggccagt aagacgctgc    3000
ccatcccaac cagcgctccc gtcgctctct cctccacggg gaagcccgtt ctggatgcag    3060
ggccagtgct cttctgggtg atcctggtgt tggttgtggt ggtcggctcc agcgccttcc    3120
tcctgtgcca ccggagggcc tgcaggaagc gaattcggca gaagctccac ctgtgctacc    3180
cggtccagac ctcccagccc aagctagagc ttgtggattc agacccaggaggagctcaa    3240 cgcagctgag gagtggtgcg tcggtgacag aacccgtcgc ggaagagcga gggttaatga    3300
gccagccact gatggagacc tgccacagcg tgggggcagc ctacctggag agcctgccgc    3360
tgcaggatgc cagcccggcc gggggccccct cgtcccccag ggaccttcct gagccccggg    3420
tgtccacgga gcacaccaat aacaagattg agaaaatcta catcatgaag gctgacaccg    3480
tgatcgtggg gaccgtgaag gctgagctgc cggagggccg gggcctggcg gggccagcag    3540
agcccgagtt ggaggaggag ctggaggcgg accatacccc ccactacccc gagcaggaga    3600
cagaaccgcc tctgggcagc tgcagcgatg tcatgctctc agtggaagag aagggaaag    3660 aagaccccttg ccacagct gcctctggaa ag                                  3692
```

<210> SEQ ID NO 31
<211> LENGTH: 244
<212> TYPE: PRT
<213> ORGANISM: Artificial Sequence
<220> FEATURE:
<223> OTHER INFORMATION: scFv VH-linker-VL

<400> SEQUENCE: 31

```
Gln Val Gln Leu Gln Gln Ser Gly Ala Glu Val Lys Lys Pro Gly Ser
1               5                   10                  15

Ser Val Lys Val Ser Cys Lys Thr Ser Gly Tyr Thr Phe Thr Gly Tyr
            20                  25                  30

Tyr Met His Trp Val Arg Gln Ala Pro Gly Gln Gly Phe Glu Trp Met
        35                  40                  45

Gly Trp Ile Asp Pro Asn Ser Gly Ala Thr Thr Tyr Ala Gln Lys Phe
    50                  55                  60

Gln Gly Arg Leu Ile Leu Ser Arg Asp Thr Ser Ile Asn Thr Ala Tyr
65                  70                  75                  80

Met Glu Leu Arg Arg Leu Thr Ser Asp Asp Thr Ala Val Tyr Tyr Cys
                85                  90                  95

Ala Lys Lys Thr Thr Gln Thr Thr Trp Gly Phe Pro Phe Trp Gly Gln
            100                 105                 110

Gly Thr Thr Val Thr Val Ser Ser Gly Gly Gly Ser Gly Gly Gly Ser
        115                 120                 125

Gly Gly Gly Ser Gly Gly Ser Asp Ile Val Met Thr Gln Ser Pro
    130                 135                 140

Ser Thr Leu Ser Ala Ser Val Gly Asp Arg Val Thr Ile Thr Cys Arg
145                 150                 155                 160

Ala Ser Gln Gly Val Tyr Gln Trp Leu Ala Trp Tyr Gln Gln Lys Pro
                165                 170                 175

Gly Lys Ala Pro Asn Leu Leu Ile Tyr Lys Ala Ser His Leu Tyr Asn
            180                 185                 190
```

```
Gly Val Pro Ser Arg Phe Ser Gly Ser Gly Ser Gly Thr Asp Phe Thr
        195                 200                 205

Leu Thr Ile Ser Ser Leu Gln Pro Asp Asp Phe Ala Thr Tyr Tyr Cys
        210                 215                 220

Gln Gln Leu Asn Ser Tyr Pro Leu Thr Phe Gly Gly Gly Thr Lys Val
225                 230                 235                 240

Glu Ile Lys Arg
```

RECOMBINANT CHIMERIC ANTIGEN RECEPTOR GENE AND USE THEREOF

CROSS-REFERENCE TO RELATED APPLICATIONS

This application is a continuation application of PCT International Application PCT/CN2018/076801, filed Feb. 14, 2018, which is incorporated by reference herein in its entirety.

FIELD OF THE INVENTION

The invention relates to the field of tumor treatment, in particular, to a recombinant chimeric antigen receptor (CAR) gene and its vector, as well as its use in tumor treatment, particularly in CD30 positive tumors.

BACKGROUND OF THE INVENTION

Hodgkin's Lymphoma (HL) is a unique type of lymphoma and one of the most common malignancies among young people. According to the epidemiological survey, the incidence of Hodgkin's Lymphoma around the world is quite different, which is prevalent in European and American countries and accounts for about 45% of lymphomas, ranking first in lymphomas; while the incidence in China and Japan is lower. The positive expression of CD30 antigen on RS cells of classical Hodgkin's Lymphoma is an important immunological marker for identifying RS cells.

Anaplastic large cell lymphoma (ALCL), an independent type of non-Hodgkin's Lymphoma (NHL), was identified by German pathologist Stein et al., in 1985 with Ki-1 (CD30) antibody and was named anaplastic large cell lymphoma. ALCL is clinically classified into two types, primary (systemic and skin) and secondary (transformed from other lymphomas), which account for about 2-7% of all NHLs.

The basic principle of CAR-T, with the full name chimeric antigen receptor T-cell immunotherapy, is to utilize the patient's own immune cells to eliminate cancer cells. The chimeric antigen receptor (CAR) consists of an extracellular antigen-binding domain, a transmembrane domain and an intracellular signaling domain. The CAR-T cell therapy technology refers to preparing a recombinant plasmid by gene recombination of the above CAR structure in vitro, and then introducing it into the patient's T cells in vitro, thereby obtaining CAR-T cells capable of expressing the above-mentioned chimeric antigen receptor. Then, after purification and large-scale expansion in vitro, the above-mentioned CAR-T cells are infused back to the body of the patient to achieve the function of killing tumor cells.

CAR-T can combine the physiological functions of T cells with the ability to recognize surface antigens in a non-MHC restricted manner. These receptors recognize intact membrane proteins independent of antigen processing. CAR-T cell therapy is to express a fusion protein of a single chain antibody fragment (scFv) that recognizes a tumor-associated specific antigen and a T cell activation sequence on the surface of T cells by exogenous gene transduction technology, which is then infused back into the patient and expanded in large amounts, exhibiting strong anti-tumor effects in a non-MHC-restricted pattern. However, the problem of the CAR is that by the intracytoplasmatic scFv-TCRζ single chain domain, the signal cannot fully replicate the multi-stranded TCR signal complex. Therefore, there is a need in the art to develop CAR genes that increase T cell function and proliferation.

SUMMARY OF THE INVENTION

The present invention provides a recombinant CAR gene, and the transfection of T lymphocytes with the recombinant CAR gene or a vector comprising the recombinant CAR gene is highly efficient, as well as the transfected positive T lymphocytes have better proliferation capability. In the present invention, the recombinant CAR constructed by using the antigen binding portion of the CD30 antibody is expressed on the surface of T cells, and can specifically kill CD30-positive tumor cells. The recombinant CAR gene of the invention has high specificity for CD30-positive tumors and promotes CAR-T to specific kill, e.g., Hodgkin's Lymphoma or anaplastic large cell lymphoma or other CD30-positive tumors.

In one aspect, the invention provides an isolated recombinant nucleic acid (CAR recombinant gene) encoding a polypeptide comprising an antigen-binding portion of a CD30 antibody, a transmembrane portion, as well as a cytoplasmic functional region of CD137 and a cytoplasmic functional region of CD3zeta linked in any order, wherein the recombinant nucleic acid optionally further comprises a nucleotide sequence encoding a signal peptide.

In one aspect, the invention provides a CAR fusion protein, comprising an antigen-binding portion of a CD30 antibody, a transmembrane portion, as well as a cytoplasmic functional region of CD137 and a cytoplasmic functional region of CD3zeta linked in any order.

In one aspect, the invention provides a recombinant T lymphocyte with a fusion polypeptide comprising an antigen-binding portion of a CD30 antibody, a transmembrane portion, as well as a cytoplasmic functional region of CD137 and a cytoplasmic functional region of CD3zeta linked in any order.

In one aspect, the invention provides a method for treating Hodgkin's lymphoma or anaplastic large cell lymphoma or another CD30 positive tumor in a patient, comprising administering to the patient a recombinant T lymphocyte with a fusion polypeptide comprising an antigen-binding portion of a CD30 antibody, a transmembrane portion, as well as a cytoplasmic functional region of CD137 and a cytoplasmic functional region of CD3zeta linked in any order.

DETAILED DESCRIPTION OF THE INVENTION

Figure 1:
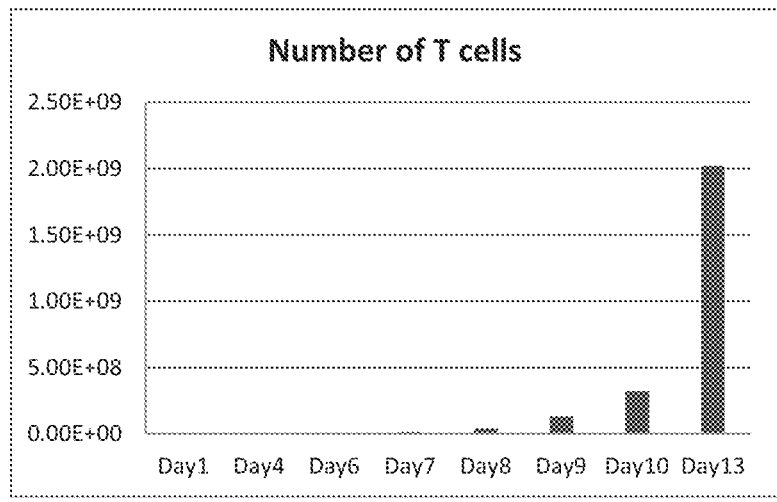
FIG. 1 shows the results of in vitro expansion of lymphocytes.

While various embodiments and aspects of the present invention have been shown and described herein, it will be obvious to those skilled in the art that these embodiments and aspects are only illustrative of the invention. The skilled artisan can make various changes and modifications without departing from the spirit of the present invention. It shall be understood that various alternatives to the embodiments of the invention described herein may also be used in the implementation of the invention.

Unless otherwise indicated or evident from the context, the abbreviations used herein have the same meanings as commonly understood by one of ordinary skill in the chemical and biological arts, and the chemical structures and formulae set forth in the examples herein should be understood in accordance with the standard rules of valences known in the art.

In one aspect, the invention provides an isolated recombinant nucleic acid (CAR recombinant gene) encoding a polypeptide comprising:

an antigen-binding portion of a CD30 antibody,
a transmembrane portion, and
a cytoplasmic functional region of CD137 and a cytoplasmic functional region of CD3zeta linked in any order,
wherein the recombinant nucleic acid optionally further comprises a nucleotide sequence encoding a signal peptide.

In one aspect, the invention provides a CAR fusion protein, comprising:

an antigen-binding portion of a CD30 antibody,
a transmembrane portion, and
a cytoplasmic functional region of CD137 and a cytoplasmic functional region of CD3zeta linked in any order.

When used in reference to a nucleic acid or protein, the term "isolated" means that the nucleic acid or protein is substantially free of other cellular components to which it binds in the native state. It may be, for example, a homogenous state, and may be dry or in aqueous solution.

As used herein, the term "recombinant," when used to refer to a cell, nucleic acid, protein or vector, means that the cell, nucleic acid, protein or vector has been modified or is the result of a laboratory method. Thus, for example, a recombinant protein comprises a protein produced by a laboratory method. Recombinant proteins may comprise an amino acid that is not found in a protein in a naturally occurring (non-recombinant) form, or may comprise an amino acid residue that is modified, such as labeled.

As used herein, the term "nucleic acid" refers to a deoxyribonucleotide or ribonucleotide and its single- or double-stranded polymer, as well as its complementary sequence. The term "polynucleotide" or "nucleotide sequence" refers to a linear sequence of nucleotides. The term "nucleotide" typically refers to a single unit of a polynucleotide, i.e., a monomer. The nucleotide can be ribonucleotide, deoxyribonucleotide or modified version thereof. Examples of the nucleotide sequence herein comprise single-stranded and double-stranded DNAs, single-stranded and double-stranded RNAs (including siRNA), and hybrid molecules having a mixture of single-stranded and double-stranded DNA and RNA. As used herein, a nucleic acid also refers to a nucleic acid having the same basic chemical structure as a naturally occurring nucleic acid. Such analog has a modified sugar and/or a modified ring substituent but retains the same basic chemical structure as a naturally occurring nucleic acid. Nucleotide mimetic refers to a compound that has a structure that is different from the general chemical structure of a nucleic acid but functions in a manner similar to a naturally occurring nucleic acid. Examples of such analog comprise, but not limited to, phosphorothioates, phosphoramides, methyl phosphonates, chiral methyl phosphonates, 2-O-methylribonucleotides, and peptide-nucleic acids (PNA).

The terms "polypeptide," "peptide," and "protein" are used interchangeably herein to refer to an amino acid residue polymer. The term applies to an amino acid polymer in which one or more amino acid residues are artificial chemical mimetics of corresponding naturally occurring amino acids, and said term also applies to a naturally occurring amino acid polymer and a non-naturally occurring amino acid polymer. The term "amino acid" refers to naturally occurring and synthetic amino acids, as well as amino acid analogs and amino acid mimetics that function in a manner similar to naturally occurring amino acids. Naturally occurring amino acids are those encoded by the genetic codons, as well as amino acids that are later modified, e.g. hydroxyproline, γ-carboxyglutamate and O-phosphoserine. Amino acid analogue refers to a compound that has the same basic chemical structure as a naturally occurring amino acid, i.e. hydrogen bonded alpha carbon, carboxyl, amino and R groups such as homoserine, norleucine, methionine sulfoxide, methionine methyl sulfonium. Amino acid mimetic refers to a compound that has a structure that is different from the general chemical structure of an amino acid but functions in a manner similar to a naturally occurring amino acid. An amino acid may be represented herein by the known three-letter symbol, or by the one-letter symbol recommended by the IUPAC-IUB Biochemical Nomenclature Commission. Similarly, a nucleotide can be represented by commonly accepted single-letter symbol.

CD30 is a membrane protein receptor located on an activated lymphocyte and is a member of the tumor necrosis factor family. It is a tumor marker of Hodgkin's Lymphoma and anaplastic large cell lymphoma. TRAF2 and TRAF5 after binding to CD30 activate the nuclear factor-kappa B pathway in the cell, leading to cell proliferation and abnormal apoptosis, inducing a tumor.

The term "antibody," as used herein, refers to a polypeptide or portion thereof specifically binding and recognizing an antigen, comprising a framework region from an immunoglobulin gene. The known immunoglobulin genes comprise the κ, λ, α, γ, δ, ε and μ constant region genes, as well as immunoglobulin variable region genes. Light chains are classified as κ or λ. Heavy chains are classified as α, γ, δ, ε or μ, which define the immunoglobulin classes, which are IgA, IgG, IgD, IgE, and IgM, respectively. Typically, the antigen-binding region of an antibody plays a significant role in determining the specificity and affinity of the binding. In some embodiments, an antibody or an antibody fragment may be derived from different organisms, including human, mouse, rat, hamster, camel and the like.

A natural antibody molecule contains two identical polypeptide chain pairs, each pair having one light chain and one heavy chain. Each light or heavy chain consists of two regions: a variable ("V") region that involved in binding a target antigen, and a constant ("C") region that interacts with other components of the immune system. The light and heavy chain variable regions together form a variable region that binds to an antigen, such as a receptor on the cell surface, in a 3-dimensional space. Within each light or heavy chain variable region, there are 3 complementarity determining regions (CDRs). These six CDRs in an antibody variable domain (3 from the light chain and 3 from the heavy chain) fold in 3 dimensional space to form the actual antibody binding site. The position and length of the CDRs have been precisely defined by Kabat, E. et al., Sequences of Proteins of Immunological Interest, U.S. Department of Health and Human Services, 1983, 1987. The portion of the variable region that is not contained in the CDR is called the framework (FR), which forms the CDR's environment.

In the invention, an antigen-binding portion has a generally known meaning to those skilled in the art and refers to a portion capable of specifically binding the target antigen. For example, an "antigen-binding portion" of an antibody can be produced by recombinant DNA technique or by enzymatic or chemical cleavage of an intact antibody, including Fab, Fab', F(ab')$_2$, Fv and single-chain antibody (scFv). The preparation or use of an antibody or a fragment thereof is well known and disclosed, for example, in Harlow, E. and Lane, D., Antibodies: A Laboratory Manual, Cold Spring Harbor Laboratory Press, Cold Spring Harbor, N.Y., 1999.

When referring to an antibody, "specific binding" refers to a binding reaction that determines the presence of an antigen, usually in a heterogeneous population of the antigen and other biological products. Thus, the antibody binds to a particular antigen at least twice the background, more typically 10-100 times the background, under an indicated assay condition. Specific binding to an antibody under such a condition typically requires an antibody that is selected based on the specificity for a particular antigen. For example, polyclonal antibodies may be selected to obtain a subset of antibodies that specifically react exclusively with the selected antigen without immunologically reacting with other substances. This selection can be achieved by removing antibodies that cross-react with other molecules. Various immunoassays can be used to select an antibody that specifically immune-reacts with a particular antigen, such as ELISA (see, e.g. Harlow & Lane, Using Antibodies, A Laboratory Manual (1998), which describes the immunoassay formats and conditions that used to determine specific immune-reactivity).

In one embodiment, the antigen binding portion of a CD30 antibody according to the invention is selected from the group consisting of the antigen binding fragments Fab, Fab', F(ab')$_2$, Fv and a single chain antibody (scFv).

In one embodiment, the heavy chain variable region (VH) of a CD30 antibody comprises the amino acid sequence set forth in SEQ ID NO: 1 and the light chain variable region (VL) comprises the amino acid sequence set forth in SEQ ID NO: 2.

It is known that digestion of an intact antibody with pepsin yields F(ab)'$_2$, which is a Fab dimer and the Fab itself is a light chain linked to VH-CH1 by a disulfide bond. F(ab)'$_2$ can be reduced under a mild condition to break the disulfide bond in the hinge region, thereby converting the F(ab)'$_2$ dimer to a Fab' monomer. The Fab' monomer is essentially an antigen-binding portion with partial hinge region (see Fundamental Immunology (Paul ed., 3d ed. 1993). Although various antibody fragments are defined based on the digestion of the intact antibody, those skilled in the art understand such fragments can be synthesized de novo by chemistry or synthesized de novo using recombinant DNA methodology. Thus, the term antigen binding portion as used herein comprises an antibody fragment produced by modifying an intact antibody or an antibody fragment synthesized de novo by recombinant DNA methodology (e.g. single-chain Fv) or an antibody fragment identified by a phage display library (see, for example, McCafferty et al., Nature 348:552-554 (1990)).

A single-chain variable fragment (scFv) is typically a fusion protein of heavy chain variable region (VH) and light chain variable region (VL) of an immunoglobulin linked by about 10 to about 25 amino acid short linker peptide. The linker is usually rich in glycine to have flexibility and has serine or threonine to have solubility. The linker can link the N-terminus of VH to the C-terminus of VL, or vice versa. The linker linking VH and VL may be any suitable linker known in the art, for example (GGGS)$_n$, where n is an integer from 1 to 10, such as 1, 2, 3, 4, 5, 6, 7, 8 or 9.

In one embodiment, the antigen binding portion of a CD30 antibody according to the invention is a single chain antibody (scFv), in which the heavy chain variable region (VH) and the light chain variable region (VL) are linked in any order directly or through a linker, for example, from N to C termini, may be: VH-VL, VL-VH, VH-linker-VL or VL-linker-VH.

In one embodiment, the antigen binding portion of a CD30 antibody according to the invention comprises or consists of, e.g., SEQ ID NO: 3 or 31.

In the invention, the terms "transmembrane portion" and "transmembrane region" can be used interchangeably and have a meaning generally known to those skilled in the art and refer to a portion of a transmembrane protein that links the extracellular region and the intracellular region of the protein. It spans the cell membrane, for example, with typically α-helical structure and about 20-25 amino acid residues. The amino acids constituting the transmembrane portion of a protein are mostly hydrophobic amino acids. The transmembrane portion described herein is capable of anchoring the protein encoded by the recombinant CAR gene provided herein and embodiments thereof in a biological membrane (e.g. cell membrane of T cell). Any transmembrane domain capable of anchoring the protein encoded by the recombinant CAR gene provided herein and embodiments thereof is comprised in the present invention.

In one embodiment, the transmembrane portion to be used in the CAR recombinant gene or CAR fusion protein according to the present invention is selected from the transmembrane portion of a CD molecule, e.g. selected from the group consisting of the transmembrane portion of CD30 molecule, the transmembrane portion of CD8 molecule, the transmembrane portion of CD28 molecule, the transmembrane portion of 41BB molecule, and the transmembrane portion of CD3zeta molecule.

In one embodiment, the transmembrane portion of a CAR recombinant gene or CAR fusion protein according to the invention is the transmembrane portion of CD8 molecule. The term "transmembrane portion of a CD molecule" as provided herein comprises the transmembrane domain of any recombinant or naturally-occurring form of a CD molecule, or variant or homolog that maintains the transmembrane domain activity of a CD molecule (e.g. at least 50%, 80%, 90%, 95%, 96%, 97%, 98%, 99% or 100% active as compared to the transmembrane domain of a CD molecule). In some aspects, said variant or homologue has at least 90%, 95%, 96%, 97%, 98%, 99% or 100% amino acid sequence identity with the transmembrane domain polypeptide of a naturally occurring CD molecule in the range of the full or partial sequence (e.g. 50, 100, 150 or 200 consecutive amino acid portion).

In one embodiment, the transmembrane domain of CD8 molecule is a protein comprising SEQ ID NO: 4 or a homologue or functional fragment thereof. In one embodiment, said transmembrane portion of CD8 molecule comprises or consists of the amino acid sequence set forth in SEQ ID NO: 4 or 5, and the nucleic acid sequence encoding the transmembrane portion of CD8 molecule comprises or consists of, for example, SEQ ID NO: 10 or 11.

In one embodiment, the transmembrane portion of the invention, e.g. the CD8 transmembrane domain is linked to the C-terminus of an antigen binding portion of a CD30 antibody, e.g. the C-terminus of a heavy chain variable region or light chain variable region).

In the invention, the terms "cytoplasmic portion" and "cytoplasmic functional region" are used interchangeably and comprise an amino acid sequence capable of providing primary signaling in response to binding of an antigen to the antigen binding portion provided in the embodiments herein, resulting in activation and/or proliferation (cell division) of T-cells expressing the CAR gene.

The cytoplasmic portion of a CAR recombinant gene or CAR fusion protein according to the invention comprises a CD137 cytoplasmic domain and a CD3zeta cytoplasmic domain.

The CD137 molecule is a member of the tumor necrosis factor receptor (TNFR) superfamily and is another important co-stimulating molecule that mediates T cell activation in addition to CD28/B7. It is mainly distributed on the surface of activated CD4-positive T cells, CD8-positive T cells, and NK cells. The cytoplasmic functional region of CD137 contains a conserved sequence of 5 amino acids that mediates the secondary signal of T cell activation. The cytoplasmic functional region of a CD137 molecule according to the invention refers to all or part of a cytoplasmic functional region of a CD137 molecule that is capable of mediating T cell activation. Preferably, said cytoplasmic functional region of a CD137 molecule comprises or consists of the amino acids set forth in SEQ ID NO: 6, and the nucleic acid sequence encoding the cytoplasmic functional region of a CD137 molecule is shown in SEQ ID NO: 12.

The CD3zeta molecule is a T cell stimulator and is also a member of the T cell co-receptor complex. The CD3 cytoplasmic portion contains three ITAMs that trigger T cell division and cytokine release. The cytoplasmic functional region of a CD3zeta molecule according to the invention refers to all or part of a cytoplasmic functional region of a CD3zeta molecule that contains the three ITAMs and can trigger T cell division and cytokine release. Preferably, the cytoplasmic functional region of a CD3zeta molecule comprises or consists of the amino acids set forth in SEQ ID NO: 7, and the nucleic acid sequence encoding the cytoplasmic domain of a CD3zeta molecule is set forth in SEQ ID NO: 13.

In the CAR recombinant gene or CAR fusion protein according to the invention, the CD137 cytoplasmic functional region and the CD3zeta cytoplasmic functional region can be linked in any order, for example, CD137 cytoplasmic functional region-CD3zeta cytoplasmic functional region, or CD3zeta cytoplasmic functional region-CD137 cytoplasmic functional region.

In one embodiment, the cytoplasmic functional regions in the CAR recombinant gene or CAR fusion protein according to the invention are linked in the order of CD137 cytoplasmic domain-CD3zeta cytoplasmic domain from the N- to C-terminus In one embodiment, the isolated recombinant nucleic acid according to the invention encodes, from 5' to 3' direction, an antigen binding portion of a CD30 antibody, such as a scFv, a transmembrane portion, and a cytoplasmic portion.

In one embodiment, the recombinant CAR gene according to the invention encodes the portions linked in the following order, from 5' to 3' direction:

a scFv of a CD30 antibody-a transmembrane portion (e.g. a CD8 transmembrane domain)-a CD137 cytoplasmic functional region-a CD3zeta cytoplasmic functional region, optionally with a spacer region between the scFV of a CD30 antibody and the transmembrane portion.

In one embodiment, the CAR recombinant gene according to the invention comprises a nucleotide sequence that encodes a spacer region located between the antigen binding portion of a CD30 antibody and the transmembrane portion, wherein the spacer region can be used for purification or other purposes.

As used herein, "spacer region" is a polypeptide that links an antigen-binding portion and a transmembrane portion. In some embodiments, the spacer region links the heavy chain constant region and the transmembrane portion. In some embodiments, the spacer region comprises an Fc region, such as an IgG Fc, an amino acid sequence set forth in SEQ ID NO: 8. Examples of the spacer region comprise, but not limited to, an immunoglobulin molecule or a fragment thereof (e.g., IgG1, IgG2, IgG3, IgG4) and an immunoglobulin molecule or a fragment thereof including a mutation that affects Fc receptor binding (e.g. IgG1, IgG2, IgG3, IgG4). In some embodiments, the spacer region is a fragment of an IgG (e.g. IgG4), wherein the fragment comprises a deletion of CH2 domain.

The spacer region can be a peptide linker. In some embodiments, the spacer region is a serine-glycine linker. In some embodiments, the spacer region has the sequence GGSG (SEQ ID NO: 14). In some embodiments, the spacer region has the sequence GSGSGSGS (SEQ ID NO: 15). In some embodiments, the spacer region is at least 4 amino acids in length. In some embodiments, the spacer region is about 4 amino acids in length. In some embodiments, the spacer region is 4 to 250 amino acids in length. The spacer region can comprise one or more residues that are capable of extending the in vivo (e.g., plasma) half-life of the protein provided herein. In some embodiments, the spacer region is 10 amino acids in length. In some embodiments, the spacer region is GGGSSGGGSG (SEQ ID NO: 16). In some embodiments, the CAR recombinant gene according to the invention does not comprise a nucleotide sequence encoding a spacer region.

In some embodiments, the isolated recombinant nucleic acid provided herein comprises a linker sequence encoding a linker domain that is located between the transmembrane portion and the intracellular domain, e.g. GGCGG (SEQ ID NO: 17) or GGG.

The term "signal peptide" as used herein refers to its ordinary meaning in the art and refers to a peptide of about 5-30 amino acids. The signal peptide is present at the N-terminus of the newly synthesized protein that is part of a secretory pathway. A protein of a secretory pathway comprise, but not limited to, a protein located within some organelles (endoplasmic reticulum, Golgi apparatus, or endosomes), a protein secreted from cells, or a protein inserted into cell membrane. In one embodiment, the signal peptide shown is, for example, MALPVTALLLPLALLL-HAARP (SEQ ID NO: 18).

In one embodiment, the isolated recombinant nucleic acid according to the invention encodes, from 5' to 3' end: a signal peptide, a heavy chain variable region sequence, optionally a linker sequence, a light chain variable region sequence, a spacer sequence, a transmembrane portion sequence, a peptide linker sequence and a cytoplasmic functional region sequence.

In one embodiment, the fusion protein according to the invention comprises, from N- to C-termini, an antigen-binding portion of a CD30 antibody, a spacer sequence, a transmembrane portion sequence, a peptide linker sequence and a cytoplasmic functional region sequence.

In one embodiment, the fusion protein according to the invention comprises, from N to C-termini, a ScFv of a CD30 antibody, a spacer sequence, a transmembrane portion sequence, a peptide linker sequence and a cytoplasmic functional region sequence.

In one embodiment, the fusion protein according to the invention comprises, from N to C-termini: (i) optionally a signal peptide, (ii) the sequence set forth in SEQ ID NO: 2, (iii) optionally a linker, (iv) the sequence set forth in SEQ ID NO: 1, (v) a transmembrane portion sequence, and (vi) a cytoplasmic functional region sequence.

In one embodiment, the fusion protein according to the invention comprises from N to C-termini: (i) optionally a signal peptide, (ii) the sequence set forth in SEQ ID NO: 3, (iii) a transmembrane portion sequence, and (iv) a cytoplasmic functional region sequence.

In one embodiment, the nucleotide sequence of a recombinant CAR gene according to the invention comprises or consists of SEQ ID NO: 20 or 21. In one embodiment, a fusion protein according to the invention comprises or consists of the amino acid sequence set forth in SEQ ID NO: 19 or 22.

In another aspect, the invention further provides a fusion polypeptide encoded by the CAR recombinant gene according to the invention.

In another aspect, the invention further provides a vector comprising the CAR recombinant gene according to the invention. Such vector comprises expression vector, plasmid, lentivirus, retroviral vector and the like. As used herein, an "expression vector" is a recombinantly or synthetically produced nucleic acid construct having a series of designated nucleic acid elements that allow the transcription of a particular nucleic acid in a host cell, e.g., in addition to encode a nucleic acid sequence to be expressed, an expression vector may further comprise a replication and control sequence that is compatible with the host that is used for expression, as well as a selection marker that confers the transfected cells a selectable phenotype. The CAR recombinant gene according to the invention may be incorporated into a plasmid, virus such as lentivirus or retroviral vector. The vector according to the invention may be a lentivirus plasmid vector, such as pLent-EF1a, or a lentivirus vector, such as LT88001 vector of Vigene Biosciences, Shandong, China.

In another aspect, the invention provides a method for preparing a recombinant T lymphocyte, comprising transforming a T lymphocyte with the CAR recombinant gene according to the invention or a recombinant vector containing the same or the CAR fusion protein according to the invention.

The term "transforming" refers to a method of introducing a nucleic acid molecule or protein into a cell. A non-viral or virus-based method may be used to introduce a nucleic acid into cell. The nucleic acid molecule can be a gene sequence that encodes an intact protein or a functional portion thereof. The non-viral transformation method comprises any suitable method that does not employ a viral DNA or viral particle as a delivery system for introducing a nucleic acid molecule into a cell. Examples of the non-viral transformation method comprise calcium phosphate transfection, lipofection, nucleofection, sonication, heat shock transfection, magnetic transfection and electroporation. In some embodiments, a nucleic acid molecule is introduced into a cell using electroporation according to standard procedures known in the art. For the virus-based transformation method, any useful viral vector can be used in the method described herein. Examples of the viral vector comprise, but not limited to, retrovirus, adenovirus, lentivirus and adeno-associated virus vectors. In some embodiments, a nucleic acid molecule is introduced into a cell by using a retroviral vector according to standard procedures known in the art. The methods for transforming a cell with a vector are well known in the art and can be found, for example, in Sambrook et al. Molecular Cloning: A Laboratory Manual (3rd ed., Cold Spring Harbor Laboratory Press, Cold Spring Harbor, N.Y. (2001)). The term "transformation" also refers to the introduction of a protein from the external environment into a cell. The protein transformation typically depends on the peptide or protein that can cross the cell membrane attached to the protein of interest, see, e.g., Ford et al. (2001) Gene Therapy 8:1-4 and Prochiantz (2007) Nat. Methods 4:119-20.

In one embodiment, the transformed T lymphocytes are expanded in vitro for at least 7 days, at least 8 days, at least 9 days, at least 10 days, at least 11 days, at least 12 days, at least 13 days, or at least 14 days. The method for culturing expanded T lymphocytes is well known to those skilled in the art, for example, see Dynabeads® Human T-Activator CD3/CD28 (Cat. Nos: 11131D, 11132D and 11161D, Life Technologies AS, Norway).

In another aspect, the invention provides a T lymphocyte having a CAR fusion protein according to the invention, e.g., on the cell membrane.

In one embodiment, the T lymphocyte can be obtained by a method of preparing a recombinant T lymphocyte according to the invention, i.e., transforming T lymphocytes with the CAR recombinant gene according to the invention or the vector containing the same, or the CAR fusion protein according to the invention, and optionally expanding in vitro, as previously described.

In another aspect, the invention provides a method of treating a CD30-positive tumor, such as Hodgkin's Lymphoma or anaplastic large cell lymphoma, in a subject, comprising administering a therapeutically effective amount of the recombinant T lymphocytes provided by the invention to a subject in need thereof.

As used herein, the term "treating" refers to remission of at least one symptom of a tumor. The term comprises administering and/or applying one or more of the recombinant genes, vectors, or T cells described herein and/or a medicament comprising the same to a subject, to provide management or treatment of a tumor. "Treatment" for the purpose of this disclosure may, but does not necessarily, provide a cure; rather, "treatment" may be a form of management of the condition. As used herein, "treating" a subject suffering from a tumor means that the tumor of the subject is partially or completely eliminated, or remains stable and no longer progresses after treatment. Treatment comprises prophylaxis, treatment and/or cure. Prophylaxis refers to prevention of the occurrence of a potential tumor and/or prevention of tumor progression or tumor development, and prevention of tumorigenesis comprises reduction or elimination of one or more risk factors leading to tumorigenesis; since it is generally impossible to determine whether a tumor has never occurred, prevention also comprises reduction of the risk of occurring or suffering from a tumor. When used to treat detrimental proliferating cells, including a cancer, "treating" comprises partially or completely destroying said detrimental proliferating cells, but with minimal disruption to normal cells.

A "patient" or "subject in need thereof," as described herein, refers to an organism that has or is susceptible to a disease or condition that can be treated by administration of a composition or pharmaceutical composition provided herein. Non-limiting examples comprise human, other mammals such as cattle, rat, mouse, dog, monkey, goat, sheep, cow, deer, and other non-mammals. In some embodiments, the patient or subject is human.

As used herein, "therapeutically effective amount" or "therapeutically effective dosage" refers to an amount of an agent, compound and material in a dose formulation at least sufficient to produce a therapeutic effect in a subject. The exact amount will depend on the purpose of the treatment and can be determined by one skilled in the art using known techniques (see, e.g., Lieberman, Pharmaceutical Dosage Forms (vols. 1-3, 1992); Lloyd, The Art, Science and Technology of Pharmaceutical Compounding (1999) Pickar, Dosage Calculations (1999); and Remington: The Science and Practice of Pharmacy, 20th Edition, 2003, Gennaro, Ed., Lippincott, Williams & Wilkins).

As used herein, the term "administration" refers to administering via any suitable route, including, for example, intravenous, intra-arteriole, intraventricular, and lymphoid tissues and the like.

In some embodiments, the method comprises administering the T lymphocyte multiple times to the patient. The dosage and intervals administered allow the CART cells to persist in vivo and kill tumor cells, and the cytokine storm after infusion is mild.

In some embodiments, the method comprises administering the T lymphocytes to the patient 2 times, 3 times, 4 times or more times, wherein each administration can be done in a suitable interval, such as 7-60 days, such as about 10, about 15, about 20, about 25, about 30, about 35, about 40, or about 50 days.

In some embodiments, the dosage of T lymphocytes administered each time is from $1\times10^5$ cells/kg body weight to $1\times10^8$ cells/kg body weight, e.g., about $5\times10^5$ cells/kg body weight, about $1\times10^6$ cells/kg body weight, about $5\times10^6$ cells/kg body weight, about $1\times10^7$ cells/kg body weight, or about $5\times10^7$ cells/kg body weight.

In some embodiments, the T lymphocytes according to the invention are autologous T lymphocytes.

In some embodiments, the T lymphocytes according to the invention are allogeneic T lymphocytes.

In one embodiment, the method of treating a CD30-positive tumor in a subject according to the invention comprises the following steps:
(i) obtaining T-lymphocytes from the subject;
(ii) transforming the T lymphocytes of step (i) with a CAR recombinant gene according to the invention or a vector containing the same, optionally expanding the transformed T lymphocytes for example for at least 7-14 days, for example at least 7 days, at least 8 days, at least 9 days, at least 10 days, at least 11 days, at least 12 days, at least 13 days, or at least 14 days; and
(iii) administering the transformed, optionally expanded, T-lymphocytes obtained in step (ii) to the subject, optionally administering multiple times to the patient, for example, each at an interval of 7-30 days, and the dosage in each time for example of approximately $1\times10^6$ cells/kg body weight.

In another aspect, the invention provides a medicament or kit for treating a CD30-positive tumor, such as Hodgkin's Lymphoma or anaplastic large cell lymphoma, comprising the CAR recombinant gene according to the invention, the CAR fusion protein according to the invention, a vector comprising the CAR recombinant gene, or the recombinant T lymphocytes according to the invention, optionally a pharmaceutically acceptable carrier.

"Pharmaceutically acceptable carrier" refers to a substance that facilitates administration of an active substance to a subject and absorption by the subject, which may be comprised in the composition according to the invention without causing significant toxic side effects to the patient. Non-limiting examples of the pharmaceutically acceptable carrier comprise water, NaCl, saline, sucrose, dextrose, binder, filler, disintegrant, lubricant, coating, sweetener, flavoring agent, saline solution, alcohol, oil, gelatin, carbohydrate such as lactose, amylose or starch, fatty acid ester, hydroxymethyl cellulose, polyvinylpyrrolidone and colorant. Those skilled in the art understand that other pharmaceutical carriers can be used in the invention.

In another aspect, the invention provides the use of the CAR recombinant gene according to the invention or a vector containing the same in the preparation of recombinant T lymphocytes.

In another aspect, the invention provides the use of the CAR recombinant gene according to the invention, the CAR fusion protein according to the invention, a vector containing the CAR recombinant gene according to the invention, or the recombinant T lymphocyte according to the invention in the preparation of a medicament or kit for treating a CD30-positive tumor such as Hodgkin's Lymphoma or anaplastic large cell lymphoma.

In another aspect, the invention provides the CAR recombinant gene according to the invention, the CAR fusion protein according to the invention, a vector containing the CAR recombinant gene according to the invention, or the recombinant T lymphocyte according to the invention, for treating a CD30 positive tumor such as Hodgkin's Lymphoma or anaplastic large cell lymphoma.

As used herein, "optionally" or "optional" means that the described following event or case occurs or does not occur, and that said description comprises instances where the event or case occurs or does not occur.

The recombinant CAR gene provided by the invention, and the vector containing the same and the T cells transformed with the recombinant CAR gene or the vector containing the same have high specificity for a CD30-positive tumor. The recombinant CAR gene was ligated into the lentivirus plasmid vector pLent-EF1a by Asis I/NsiI double digestion to construct a CART-30 scFv plasmid, which was used for packaging and purification of the lentivirus, and the recombinant CAR gene was expressed on the T cells of the patient by the lentivirus vector technology. The transfection efficiency of said CAR-T cells was high and reached 64.7%. The transfected positive T cells had a good proliferative capacity. After being expanded in vitro for about 2 weeks, the CD3 positive T cells increased 560 times.

The invention is further described below by specific examples, but the invention is not limited to the following examples.

In the invention, the term "Nluc-P2A-CD30" nucleotide sequence refers to a nucleotide sequence encoding a Nanoluc® Luciferase gene, P2A gene, and CD30 gene from 5' to 3', wherein the nucleotide sequence of CD30-encoding gene is e.g. as set forth in SEQ ID NO: 27, the nucleotide sequence of P2A encoding gene is e.g. as set forth in SEQ ID NO: 28, and the nucleotide sequence of the Nanoluc® Luciferase encoding gene is e.g. as set forth in SEQ ID NO: 29; the term "pLent-EF1a-Nluc-P2A-Puro-CMV-CD30" refers to the lentiviral vector Plent-EF1α-Puro-CMV into which the Nanoluc® Luciferase, P2A and CD30 coding sequences have been inserted; the term "ddH2O" refers to double distilled water; the term "FBS" means fetal bovine serum; the term "PEI" refers to polyethyleneimine.

In the invention, Plent-EF1α-Puro-CMV vector and ADV-HR transfection reagent were purchased from Vigene Biosciences; restriction enzymes Asis I and MluI and T4

DNA ligase were purchased from NEB; DNA Gel Recovery kit was purchased from Axygen; luminescence detector, Nano-Glo™ luciferase assay kit were purchased from Promega; HEK293, HEK293T cells were purchased from ATCC; DMEM medium was purchased from Hyclone; plasmids PMD2G and PSPAX2 were purchased from Invitrogen; lysis buffer was Nano-Glo® Luciferase Assay, purchased from Promega.

Nucleotide sequence synthesis was completed by GenScript. For those techniques or conditions that are not indicated specifically in the examples, the techniques or conditions are done according to those described in the literature in the art (for example, Sambrook (2001), Molecular Cloning: A Laboratory Manual, Cold Spring Harbor Laboratory Press; 3rd edition) or follow the product instructions.

EXAMPLES

Examples 1

Construction of the Plasmid CART-30 scFv

The method for obtaining the plasmid CART-30 scFv: designing the coding nucleotide sequences of the scFvs of the three CD30 antibodies (including the CD8a signal peptide coding sequence (SEQ ID NO: 26) and the scFv fragment coding sequences set forth in SEQ ID NOs: 23, 24 and 25, respectively) and ligating to the sequences set forth in SEQ ID NOs: 11, 12 and 13 to form 3 CAR genes:

CAR1: consisting of SEQ ID NOs: 26, 23, 11, 12 and 13;
CAR2: consisting of SEQ ID NOs: 26, 24, 11, 12 and 13; and
CAR3: consisting of SEQ ID NOs: 26, 25, 11, 12 and 13 (SEQ ID NO:21).

Figure 4:
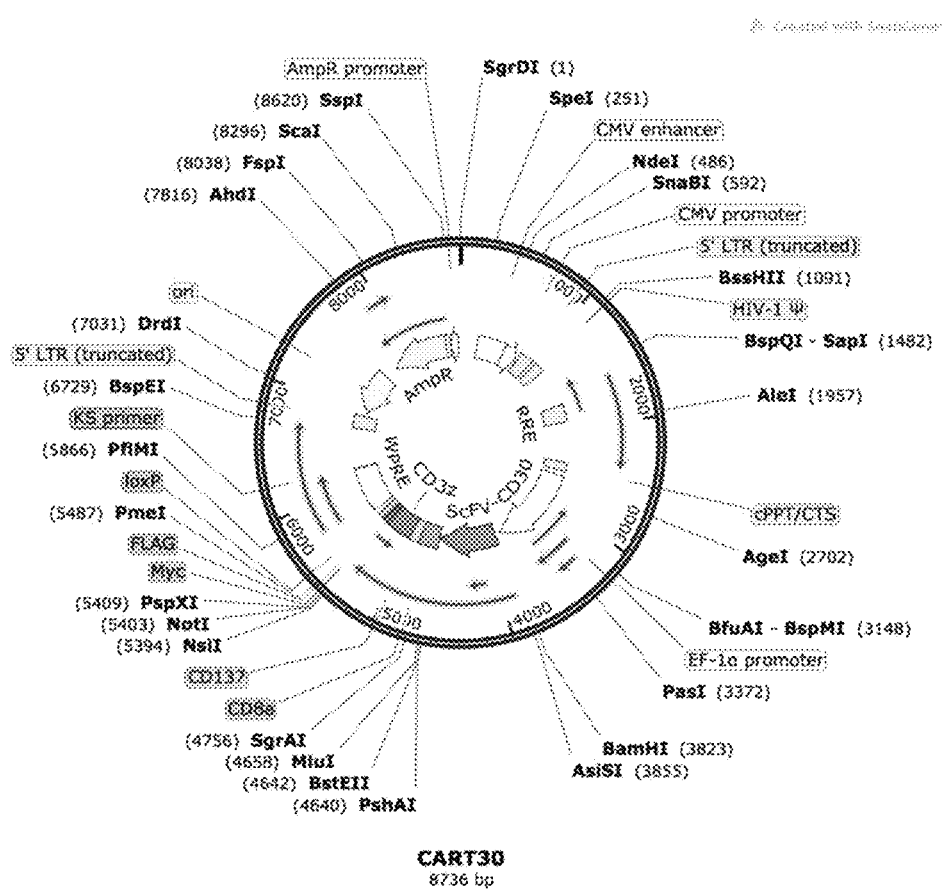
FIG. 4 is a map of the CART-30 scFv plasmid vector.
Figure 5:
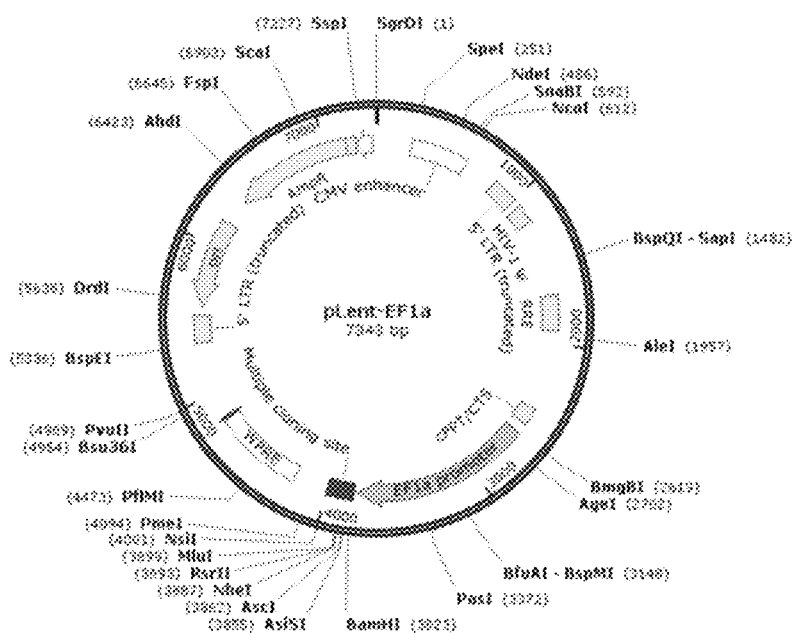
FIG. 5 s a map of the pLent-EF1a plasmid vector.

The complete sequences of the recombinant CAR1-3 genes were synthesized (GenScript), and was ligated into the lentiviral plasmid vector pLent-EF1a (Vigene Biosciences) by digestion with AsisI/NsiI (NEB Corporation). The plasmid maps of the constructed CART-30 scFv plasmid and pLent-EF1a are shown in FIG. 4 and FIG. 5.

Example 2

T Lymphocyte Transfection

Figure 2:
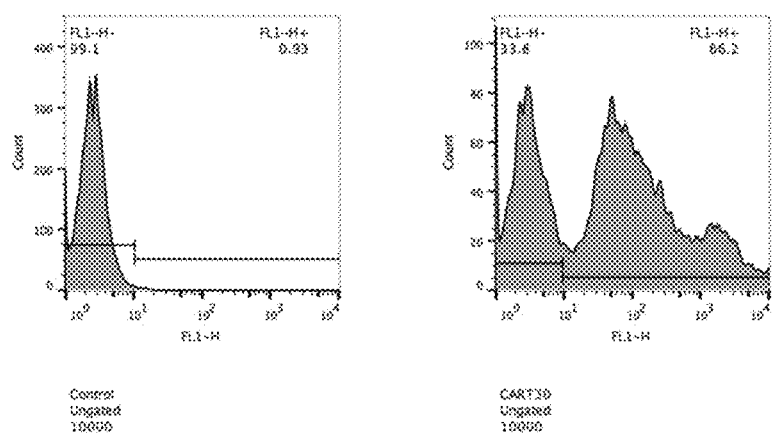
FIG. 2 is a flow cytometry plot of infection of primary T cells, showing an infection efficiency of approximately 64.7%.
Figure 3:
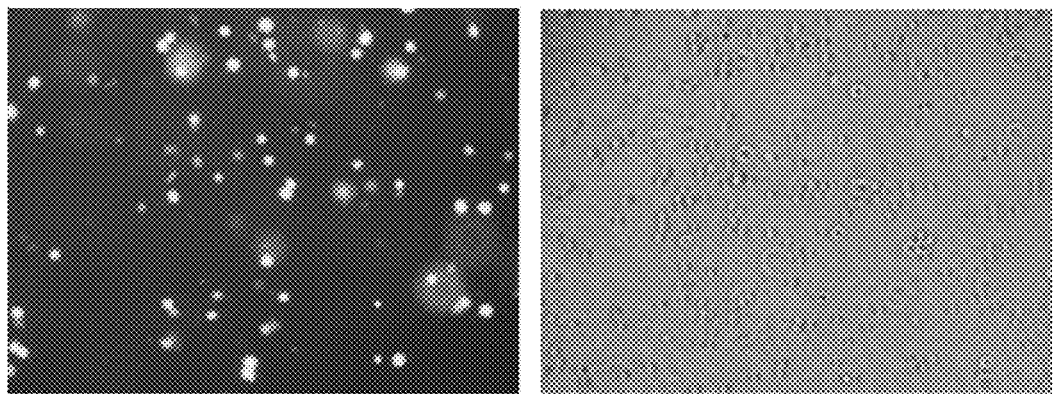
FIG. 3 shows the results of infection of primary cultured T cells with lentivirus. The left panel shows an immunofluorescence image and the right panel shows a bright field image. The infection efficiency is about 60%.

The CART-30 scFv plasmids constructed in Example 1 were subjected to lentivirus packaging and purification, and the recombinant CAR genes were expressed on T lymphocytes by lentiviral vector technology (see Tumaini B, Lee D W, Lin T, Castiello L, et al. Simplified process for the production of anti-CD19-CAR engineered T cells. Cytotherapy. 2013; 15(11): 1406-1415), and the positive infection efficiency was detected by flow cytometry. The results are shown in FIGS. 2 and 3. The transfection efficiency of T lymphocytes with the lentivirus is approximately 60%.

Example 3

In Vitro Detection of Killing Efficiency

1. Construction of CAR-T cytotoxicity indicator vector: Constructed according to the method described in Chinese Patent Application No. 201610537806.3. Briefly:
(1) Synthesizing a nucleotide sequence encoding Nanoluc® Luciferase, P2A and CD30 (SEQ ID NO: 30), and introducing AsisI and MluI restriction sites upstream and downstream, respectively;
(2) digesting the Plent-EF1α-Puro-CMV vector and the Nanoluc® Luciferase-P2A-CD30 sequence obtained in step (1) with Asis I and MluI at 37° C., and recovering the digested Nanoluc® Luciferase-P2A-CD30 sequence and Plent-EF1α-Puro-CMV vector using a DNA gel recovery kit;
(3) ligating the digested Nanoluc® Luciferase-P2A-CD30 sequence and Plent-EF1α-Puro-CMV vector at 22° C. for 2 hours, and transforming the ligation product into E. coli DH5α competent cells to obtain the cytotoxicity indicator vector pLent-EF1a-Nluc-P2A-Puro-CMV-CD30.

2. In Vitro Toxicity Testing

Figure 6:
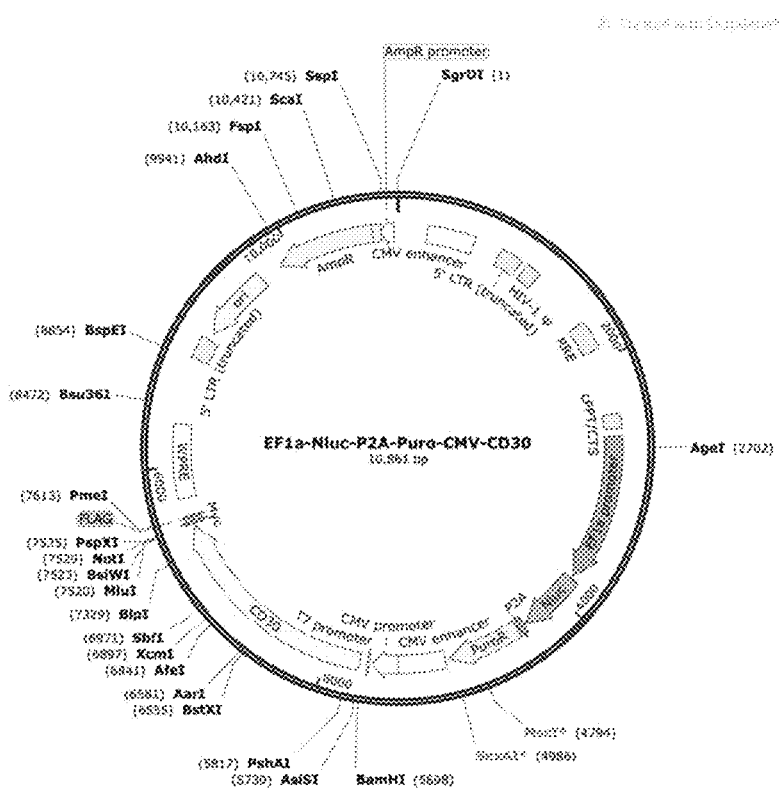
FIG. 6 is a map of pLent-EF1a-Nluc-P2A-Puro-CMV-CD30 lentivirus plasmid.

The obtained pLent-EF1a-Nluc-P2A-Puro-CMV-CD30 lentivirus plasmid map is shown in FIG. 6. On the following day after the cells were passaged, the pLent-EF1a-Nluc-P2A-Puro-CMV-CD30 plasmid was transfected into HEK293 cell line, and was plated onto 96-well plates on the third day, $10^4$ cells per well.

Each CART-30 effector cell obtained in Example 2 and pLent-EF1a-Nluc-P2A-Puro-CMV-CD30 plasmid were transfected into HEK293 cells in three concentration ratios: 10:1, 2:1, and 0:1. The reaction time was 18 hours. After centrifugation, the nanoluc value of the supernatant was measured using a fluorophotometer Luminometer, and then the nanoluc value of the precipitate was measured. The killing efficiency was calculated according to the following equation: supernatant nanoluc value/(supernatant nanoluc value+precipitate nanoluc value)×100%.

TABLE 1

Killing effect of CAR-T cells on CD30 positive cells

| CAR gene expressed | Killing Efficiency (%) |
|---|---|
| CAR1 | 45 |
| CAR2 | 30 |
| CAR3 | 76 |

The results showed that the CAR-T cells containing the recombinant CAR3 gene according to the invention could specifically recognize the CD30 antigen, and have a stronger killing efficiency to CD30-positive cells, reaching more than 60%, showing a great potential in the cell immunotherapy of tumors.

Example 4

Detection of In Vitro Proliferation Capability of Transfected T Lymphocytes

The T lymphocytes transfected with the CAR3 recombinant gene obtained in Example 2 (CAR-T cells) were expanded in vitro for 2 weeks (Dynabeads® Human T-Activator CD3/CD28 (Cat. Nos: 11131D, 11132D and 11161D, Life Technologies) AS, Norway)), and the result is shown in FIG. 1. As can be seen from the figure, T cells were expanded 560-fold after 13 days of transfection.

Example 5

Treatment of CD30-Positive Lymphoma with the CAR-T Cells

A total of 20 volunteer patients with clinically confirmed CD30 positive Hodgkin's Lymphoma were screened. All volunteer patients (aged >18, life expectancy >12 weeks, after test, creatinine <2.5 mg/dl, ALT/AST <3× normal value, bilirubin <2.0 mg/dl) had sufficient intravenous access for performing plasmapheresis and there were no other contraindications to leukapheresis. Informed consent was obtained from all patients participating in clinical trials.

The volunteer patient was given 5 days of chemotherapy before injection of CAR-T cells. The purpose of chemotherapy was to reduce the lymphocytes to promote the transplant survival rate and homeostatic expansion of CAR-T cell, and also reduce the tumor burden. The choice of chemotherapy regimen was based on the patient's underlying disease and prior treatment. CAR-T cells were given 1-2 days after the completion of chemotherapy.

The specific protocol for using CAR-T cell therapy was as follows: 50-100 ml of peripheral blood from volunteer patients was collected in heparin anticoagulant tubes, and then mononuclear cells were isolated. The patients' T cells were infected with the lentivirus containing the CAR3 recombinant gene of Example 1 and after 1-2 weeks of extensive expansion in vitro, approximately $2.5-5 \times 10^9$ autologous T cells were obtained, and the resulting CAR-T cells were then infused to the patient.

The first dosage of approximately $1 \times 10^6$/kg body weight of CART cells was given in split dosages on day 0 (10%), day 1 (30%), and day 2 (60%). If tolerated, the infusion was completed in about 10-15 minutes. Subjects' vital signs and the degree of blood oxygen saturation were monitored every 15 minutes prior to administration and after the completion of infusion, and within 1 hour after the completion of the infusion, until the indicators were stable and normal. A blood sample was collected before infusion and 20 min after the completion of the infusion to determine the baseline level of CAR-T. Before the first infusion and 2 hours after each infusion, blood potassium and blood uric acid values need to be measured. After infusion, the cytokines interferon gamma, interleukin 2 and interleukin 6 were tested weekly and QPCR quantitative detection of CART DNA content was performed.

If the patient was tolerated for the first dosage, the second and third infusions of CAR-T cells would be performed on day 30 and day 60. The dosages were approximately $1 \times 10^6$ CART cells/kg body weight. Blood was taken 2 hours after infusion to detect blood potassium and blood uric acid. After infusion, the cytokines interferon gamma, interleukin 2 and interleukin 6 were tested weekly and the QPCR quantitative detection of CART DNA content was performed.

If the prepared CART cells were sufficient, and the patient responded to CART cells, the tumor appeared to shrink significantly within one month after the first infusion, and more infusions would be performed until the CART cells were used up. The total dosage was divided into multiple $1 \times 10^6$ CART cells/kg body weight through multiple infusions at an interval of one month, allowing CART cells to persist in the body and continuously killing tumor cells, and the main advantage is the cytokine storm after infusion was very mild and patients could complete the infusion at the clinic, avoiding the high costs of repeated hospitalization.

The subjects returned to the hospital once a month for 2-6 months after infusion of CAR-T cells. In these follow-up studies, the subjects received: concomitant medication, physical examination, recording adverse events, blood test for hematology and biochemistry, survival rate of CAR-T cells, and PETCT for detecting tumor size change.

The subjects underwent quarterly assessment within 2 years after infusion. During these follow-up studies, the subjects received: concomitant medication, physical examination, recording of adverse events, and blood test for hematology and biochemistry, and survival rate of CAR-T cells.

Figure 7:
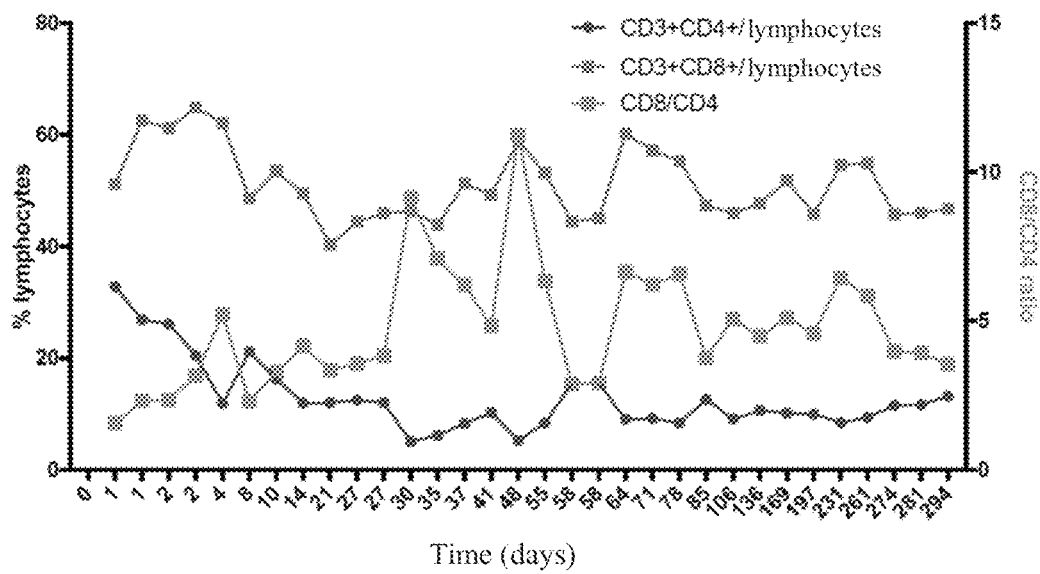
FIG. 7 shows the ratio of CD8-positive T cells/CD4-positive T cells after infusion of CART cells in patients, with the highest CD8/CD4 ratio being approximately 11.

RESULTS: in normal human blood, the regulatory T cells were CD4-positive and killer T-cells were CD8-positive, CD8/CD4 positive cells at a ratio of approximately 1:2, while in the patients infused with CART cells, the proportion of CD8-positive T cells was significantly increased, and the highest CD8/CD4 ratio was 11, as shown in FIG. 7.

Evaluating the symptom remission of volunteer patients with Hodgkin's Lymphoma within 2 years. The results were shown in Table 2.

TABLE 2

Therapeutic effects of CAR-T cells on CD30 positive Hodgkin's Lymphoma

| group | Cases | Cases of complete remission | complete remission (%) |
|---|---|---|---|
| Hodgkin's Lymphoma | 20 | 14 | 70.0 |

The results showed that the patients with CD30 positive Hodgkin's Lymphoma treated with the CAR-T cells containing the recombinant CAR3 gene according to the invention exhibited a significant therapeutic effect, and the complete symptom remission rate was as high as 70%.

The invention claimed is:

1. A product, which is a fusion polypeptide encoded by an isolated recombinant nucleic acid comprising nucleotide sequences encoding from 5' to 3' an antigen-binding portion of a CD30 antibody-a transmembrane portion-a cytoplasmic functional region of CD137-a cytoplasmic functional region of CD3zeta,
   wherein the recombinant nucleic acid comprises or consists of the sequence set forth in SEQ ID NO: 20 or 21, and
   wherein the antigen binding portion of a CD30 antibody is an scFv.

2. A product, which is a fusion polypeptide encoded by an isolated recombinant nucleic acid comprising nucleotide sequences encoding from 5' to 3' an antigen-binding portion of a CD30 antibody-a transmembrane portion-a cytoplasmic functional region of CD137-a cytoplasmic functional region of CD3zeta,
   wherein the fusion polypeptide comprises or consists of the sequence set forth in SEQ ID NO: 19 or 22, and
   wherein the antigen binding portion of a CD30 antibody is an scFv.

* * * * *